US010557156B2

United States Patent
Chung et al.

(10) Patent No.: US 10,557,156 B2
(45) Date of Patent: Feb. 11, 2020

(54) BACTERIUM CONSTITUTIVELY PRODUCING MONOPHOSPHORYL LIPID A AND METHOD OF PRODUCING MONOPHOSPHORYL LIPID A BY USING BACTERIUM

(71) Applicant: KOREA INSTITUTE OF SCIENCE AND TECHNOLOGY, Seoul (KR)

(72) Inventors: Hak Suk Chung, Seoul (KR); Yu Hyun Ji, Seoul (KR); Jin Su An, Seoul (KR); Ick Chan Kwon, Seoul (KR); Eun Gyeong Yang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/026,796

(22) Filed: Jul. 3, 2018

(65) Prior Publication Data

US 2019/0010528 A1 Jan. 10, 2019

(30) Foreign Application Priority Data

Jul. 5, 2017 (KR) ........................ 10-2017-0085406

(51) Int. Cl.
| C12P 19/12 | (2006.01) |
| C12N 9/16 | (2006.01) |
| C12N 9/14 | (2006.01) |
| C12P 7/64 | (2006.01) |

(52) U.S. Cl.
CPC ............... *C12P 19/12* (2013.01); *C12N 9/14* (2013.01); *C12N 9/16* (2013.01); *C12P 7/6436* (2013.01); *C12Y 301/03* (2013.01); *C12Y 301/03027* (2013.01); *C12Y 306/01027* (2013.01)

(58) Field of Classification Search
CPC ................. C12P 19/12; C12Y 301/03; C12Y 306/01027; C12Y 301/03027; C12N 9/16; C12N 9/14
See application file for complete search history.

(56) References Cited

U.S. PATENT DOCUMENTS

2013/0230555 A1    9/2013 Trent et al.

FOREIGN PATENT DOCUMENTS

KR    10-2016-0028870 A    3/2016

OTHER PUBLICATIONS

Chen et al. Biotechnology Letters 33:1013-1019, 2011.*
Touze et al., Molecular Microbiology 67(2):264-277, 2008.*
El Ghachi et al., The Journal Biological Chemistry 280(19):18689-18695, 2005.*
Reynolds et al., Biochemistry 48:9627-9640, 2009.*
Bishop, R., Molecular Microbiology 57(4):900-912, 2005.*
Sousa et al., Microbiology 148(Pt5):1291-1303, 2002.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Wang et al., PLoS One 10(12):e0144714, pp. 1-15, 2015.*
Bligh et al., "A Rapid Method of Total Lipid Extraction and Purification", Canadian Journal of Biochemistry and Physiology, Aug. 1959, vol. 37, No. 8, pp. 911-917.
Chung et al., "Interchangeable Domains in the Kdo Transferases of *Escherichia coli* and *Haemophilus influenzae*", Biochemistry, 2010, vol. 49, pp. 4126-4137.
Datsenko et al., "One-step inactivation of chromosomal genes in *Escherichia coli* K-12 using PCR products", PNAS, Jun. 6, 2000, vol. 97, No. 12, pp. 6640-6645.
Guzman et al., "Tight Regulation, Modulation, and High-Level Expression by Vectors Containing the Arabinose $P_{BAD}$ Promoter", Journal of Bacteriology, Jul. 1995, vol. 177, No. 14, pp. 4121-4130.
Wang et al., "Construction of versatile low-copy-number vectors for cloning, sequencing and gene expression in *Escherichia coli*", Gene, 1991, vol. 100, pp. 195-199.
Yu et al., "An efficient recombination system for chromosome engineering in *Eschericia coli*", PNAS, May 23, 2000, vol. 97, No. 11, pp. 5978-5983.
English translation of International Search Report and Written Opinion dated Feb. 15, 2019, in PCT/KR2018/007526 (Forms PCT/ISA/220, PCT/ISA/210, and PCT/ISA/237).
Han et al., "Construction of Monophosphoryl Lipid a Producing *Escherichia coli* Mutants and Comparison of Immuno-Stimulatory Activities of Their Lipopolysaccharides," Marine Drugs (2013), vol. 11, 363-376.

* cited by examiner

Primary Examiner — Delia M Ramirez
(74) Attorney, Agent, or Firm — Birch, Stewart, Kolasch & Birch, LLP

(57) ABSTRACT

A bacterium that constitutively produces monophosphoryl lipid A (MLA) and a method of producing MLA by using the bacterium may simply produce MLA and a derivative thereof without acid hydrolysis, reduce a probability of natural mutation, and increase yields of MLA and a derivative thereof by constitutive expression of the MLA and derivative thereof.

20 Claims, 7 Drawing Sheets

Specification includes a Sequence Listing.

SEQUENCE LISTING

<160> NUMBER OF SEQ ID NOS: 25

<210> SEQ ID NO 1

<211> LENGTH: 306
<212> TYPE: PRT
<213> ORGANISM: Artificial Sequence
<220> FEATURE:
<223> OTHER INFORMATION: Escherichia coli LpxL polypeptide

<400> SEQUENCE: 1

Met Thr Asn Leu Pro Lys Phe Ser Thr Ala Leu Leu His Pro Arg Tyr
1               5                   10                  15

Trp Leu Thr Trp Leu Gly Ile Gly Val Leu Trp Leu Val Val Gln Leu
            20                  25                  30

Pro Tyr Pro Val Ile Tyr Arg Leu Gly Cys Gly Leu Gly Lys Leu Ala
        35                  40                  45

Leu Arg Phe Met Lys Arg Ala Lys Ile Val His Arg Asn Leu Glu
    50                  55                  60

Leu Cys Phe Pro Glu Met Ser Glu Gln Gly Arg Arg Lys Met Val Val
65                  70                  75                  80

Lys Asn Phe Glu Ser Val Gly Met Gly Leu Met Glu Thr Gly Met Ala
                85                  90                  95

Trp Phe Trp Pro Asp Arg Arg Ile Ala Arg Trp Thr Glu Val Ile Gly
            100                 105                 110

Met Glu His Ile Arg Asp Val Gln Ala Gln Lys Arg Gly Ile Leu Leu
        115                 120                 125

Val Gly Ile His Phe Leu Thr Leu Glu Leu Gly Ala Arg Gln Phe Gly
    130                 135                 140

Met Gln Glu Pro Gly Ile Gly Val Tyr Arg Pro Asn Asp Asn Pro Leu
145                 150                 155                 160

Ile Asp Trp Leu Gln Thr Trp Gly Arg Leu Arg Ser Asn Lys Ser Met
                165                 170                 175

Leu Asp Arg Lys Asp Leu Lys Gly Met Ile Lys Ala Leu Lys Lys Gly
            180                 185                 190

Glu Val Val Trp Tyr Ala Pro Asp His Asp Tyr Gly Pro Arg Ser Ser
        195                 200                 205

Val Phe Val Pro Leu Phe Ala Val Glu Gln Ala Ala Thr Thr Thr Gly
    210                 215                 220

Thr Trp Met Leu Ala Arg Met Ser Gly Ala Cys Leu Val Pro Phe Val
225                 230                 235                 240

Pro Arg Arg Lys Pro Asp Gly Lys Gly Tyr Gln Leu Ile Met Leu Pro
                245                 250                 255

Pro Glu Cys Ser Pro Pro Leu Asp Asp Ala Glu Thr Thr Ala Ala Trp
            260                 265                 270

Met Asn Lys Val Val Glu Lys Cys Ile Met Met Ala Pro Glu Gln Tyr
        275                 280                 285

Met Trp Leu His Arg Arg Phe Lys Thr Arg Pro Glu Gly Val Pro Ser
    290                 295                 300

Arg Tyr
305

<210> SEQ ID NO 2
<211> LENGTH: 921
<212> TYPE: DNA
<213> ORGANISM: Artificial Sequence
<220> FEATURE:
<223> OTHER INFORMATION: Polynucleotide encoding Escherichia coli LpxL
      polypeptide

<400> SEQUENCE: 2

```
atgacgaatc tacccaagtt ctccaccgca ctgcttcatc cgcgttattg gttaacctgg    60
ttgggtattg cgtactttg gttagtcgtg caattgccct acccggttat ctaccgcctc   120
ggttgtggat taggaaaact ggcgttacgt tttatgaaac gacgcgcaaa aattgtgcat   180
cgcaacctgg aactgtgctt cccggaaatg agcgaacaag aacgccgtaa atggtggtg   240 aagaatttcg aatccgttgg catgggcctg atggaaaccg gcatggcgtg ttctggccg   300 gaccgccgaa tcgcccgctg gacggaagtg atcggcatgg aacacattcg tgacgtgcag   360
gcgcaaaaac gcggcatcct gttagttggc atccattttc tgacactgga gctgggtgcg   420
cggcagtttg gtatgcagga accgggtatt ggcgtttatc gcccgaacga taatccactg   480
attgactggc tacaaacctg ggccgtttg cgctcaaata aatcgatgct cgaccgcaaa   540
gatttaaaag gcatgattaa agccctgaaa aaggcgaag tggtctggta cgcaccggat   600
catgattacg gcccgcgctc aagcgttttc gtcccgttgt ttgccgttga gcaggctgcg   660
accacgaccg gaacctggat gctggcacga atgtccggcg catgtctggt gcccttcgtt   720
ccacgccgta agccagatgg caaagggtat caattgatta tgctgccgcc agagtgttct   780
ccgccactgg atgatgccga aactaccgcc gcgtggatga acaaagtggt cgaaaaatgc   840
atcatgatgg caccagagca gtatatgtgg ttacaccgtc gctttaaaac acgcccggaa   900
ggcgttcctt cacgctatta a                                             921
```

<210> SEQ ID NO 3
<211> LENGTH: 48
<212> TYPE: DNA
<213> ORGANISM: Artificial Sequence
<220> FEATURE:
<223> OTHER INFORMATION: LpxL forward primer P1

<400> SEQUENCE: 3

```
cgcagtctag aaaggagata tattgatgac gaatctaccc aagttctc              48
```

<210> SEQ ID NO 4
<211> LENGTH: 67
<212> TYPE: DNA
<213> ORGANISM: Artificial Sequence
<220> FEATURE:
<223> OTHER INFORMATION: LpxL reverse primer P2

<400> SEQUENCE: 4

```
cgctattatt ttttttcgtt tccattggta tatctccttc ttattaatag cgtgaaggaa    60
cgccttc                                                               67
```

<210> SEQ ID NO 5
<211> LENGTH: 323
<212> TYPE: PRT
<213> ORGANISM: Artificial Sequence
<220> FEATURE:
<223> OTHER INFORMATION: Escherichia coli LpxM polypeptide
<400> SEQUENCE: 5

```
Met Glu Thr Lys Lys Asn Asn Ser Glu Tyr Ile Pro Glu Phe Asp Lys
1               5                   10                  15

Ser Phe Arg His Pro Arg Tyr Trp Gly Ala Trp Leu Gly Val Ala Ala
            20                  25                  30

Met Ala Gly Ile Ala Leu Thr Pro Pro Lys Phe Arg Asp Pro Ile Leu
        35                  40                  45

Ala Arg Leu Gly Arg Phe Ala Gly Arg Leu Gly Lys Ser Ser Arg Arg
    50                  55                  60
```

Arg Ala Leu Ile Asn Leu Ser Leu Cys Phe Pro Glu Arg Ser Glu Ala
65                  70                  75                  80

Glu Arg Glu Ala Ile Val Asp Glu Met Phe Ala Thr Ala Pro Gln Ala
            85                  90                  95

Met Ala Met Met Ala Glu Leu Ala Ile Arg Gly Pro Glu Lys Ile Gln
        100                 105                 110

Pro Arg Val Asp Trp Gln Gly Leu Glu Ile Ile Glu Glu Met Arg Arg
    115                 120                 125

Asn Asn Glu Lys Val Ile Phe Leu Val Pro His Gly Trp Ala Val Asp
130                 135                 140

Ile Pro Ala Met Leu Met Ala Ser Gln Gly Gln Lys Met Ala Ala Met
145                 150                 155                 160

Phe His Asn Gln Gly Asn Pro Val Phe Asp Tyr Val Trp Asn Thr Val
                165                 170                 175

Arg Arg Arg Phe Gly Gly Arg Leu His Ala Arg Asn Asp Gly Ile Lys
            180                 185                 190

Pro Phe Ile Gln Ser Val Arg Gln Gly Tyr Trp Gly Tyr Tyr Leu Pro
        195                 200                 205

Asp Gln Asp His Gly Pro Glu His Ser Glu Phe Val Asp Phe Phe Ala
    210                 215                 220

Thr Tyr Lys Ala Thr Leu Pro Ala Ile Gly Arg Leu Met Lys Val Cys
225                 230                 235                 240

Arg Ala Arg Val Val Pro Leu Phe Pro Ile Tyr Asp Gly Lys Thr His
                245                 250                 255

Arg Leu Thr Ile Gln Val Arg Pro Pro Met Asp Asp Leu Leu Glu Ala
            260                 265                 270

Asp Asp His Thr Ile Ala Arg Arg Met Asn Glu Glu Val Glu Ile Phe
    275                 280                 285

Val Gly Pro Arg Pro Glu Gln Tyr Thr Trp Ile Leu Lys Leu Leu Lys
290                 295                 300

Thr Arg Lys Pro Gly Glu Ile Gln Pro Tyr Lys Arg Lys Asp Leu Tyr
305                 310                 315                 320

Pro Ile Lys

<210> SEQ ID NO 6
<211> LENGTH: 972
<212> TYPE: DNA
<213> ORGANISM: Artificial Sequence
<220> FEATURE:
<223> OTHER INFORMATION: Polynucleotide encoding Escherichia coli LpxM
      polypeptide

<400> SEQUENCE: 6
atggaaacga aaaaaaataa tagcgaatac attcctgagt ttgataaatc ctttcgccac    60
ccgcgctact ggggagcatg gctgggcgta gcagcgatgg cgggtatcgc tttaacgccg   120
ccaaagttcc gtgatcccat tctggcacgg ctggacgtt tgccggacg actgggaaaa    180 agctcacgcc gtcgtgcgtt aatcaatctg tcgctctgct ttccagaacg tagtgaagct   240
gaacgcgaag cgattgttga tgagatgttt gccaccgcgc cgcaagcgat ggcaatgatg   300
gctgagttgg caatacgcgg gccggagaaa attcagccgc gcgttgactg gcaagggctg   360
gagatcatcg aagagatgcg gcgtaataac gagaaagtta ctttctggt gccgcacggt   420 tgggccgtcg atattcctgc catgctgatg gcctcgcaag gcagaaaat ggcagcgatg   480 ttccataatc agggcaaccc ggttttgat tatgtctgga acacggtgcg tcgtcgcttt   540

```
ggcggtcgtc tgcatgcgag aaatgacggt attaaaccat tcatccagtc ggtacgtcag      600
gggtactggg gatattattt acccgatcag gatcatggcc cagagcacag cgaatttgtg      660
gatttctttg ccacctataa agcgacgttg cccgcgattg gtcgtttgat gaaagtgtgc      720
cgtgcgcgcg ttgtaccgct gtttccgatt tatgatggca agacgcatcg tctgacgatt      780
caggtgcgcc caccgatgga tgatctgtta gaggcggatg atcatacgat tgcgcggcgg      840
atgaatgaag aagtcgagat ttttgttggt ccgcgaccag aacaatacac ctggatacta      900
aaattgctga aaactcgcaa accgggcgaa atccagccgt ataagcgcaa agatctttat      960
cccatcaaat aa                                                         972

<210> SEQ ID NO 7
<211> LENGTH: 67
<212> TYPE: DNA
<213> ORGANISM: Artificial Sequence
<220> FEATURE:
<223> OTHER INFORMATION: LpxM forward primer P3

<400> SEQUENCE: 7
gaaggcgttc cttcacgcta ttaataagaa ggagatatac caatggaaac gaaaaaaaat      60
aatagcg                                                               67

<210> SEQ ID NO 8
<211> LENGTH: 37
<212> TYPE: DNA
<213> ORGANISM: Artificial Sequence
<220> FEATURE:
<223> OTHER INFORMATION: LpxM reverse primer P3

<400> SEQUENCE: 8
gcagaagctt ttatttgatg ggataaagat ctttgcg                              37

<210> SEQ ID NO 9
<211> LENGTH: 29
<212> TYPE: DNA
<213> ORGANISM: Artificial Sequence
<220> FEATURE:
<223> OTHER INFORMATION: PL promoter nucleotide sequence

<400> SEQUENCE: 9
ttgacataaa taccactggc ggtgatact                                       29

<210> SEQ ID NO 10
<211> LENGTH: 77
<212> TYPE: DNA
<213> ORGANISM: Artificial Sequence
<220> FEATURE:
<223> OTHER INFORMATION: Forward primer amplifying PL promoter

<400> SEQUENCE: 10
ggcagtgagc gcaacgcaga attcttgaca taaataccac tggcggtgat actttcacac      60
aggaaacagc tatgacc                                                    77

<210> SEQ ID NO 11
<211> LENGTH: 77
<212> TYPE: DNA
<213> ORGANISM: Artificial Sequence
<220> FEATURE:
<223> OTHER INFORMATION: Reverse primer amplifying PL promoter

<400> SEQUENCE: 11
```

```
ggtcatagct gtttcctgtg tgaaagtatc accgccagtg gtatttatgt caagaattct    60
gcgttgcgct cactgcc                                                   77
```

<210> SEQ ID NO 12
<211> LENGTH: 190
<212> TYPE: PRT
<213> ORGANISM: Artificial Sequence
<220> FEATURE:
<223> OTHER INFORMATION: Helicobactor pylori LpxE mutant

<400> SEQUENCE: 12

```
Met Lys Lys Phe Leu Phe Lys Gln Lys Phe Cys Glu Ser Leu Pro Lys
1               5                   10                  15

Ser Phe Ser Lys Thr Leu Leu Ala Leu Ser Leu Gly Leu Ile Leu Leu
            20                  25                  30

Gly Ile Phe Ala Pro Phe Pro Lys Val Pro Lys Gln Pro Ser Val Pro
        35                  40                  45

Leu Met Phe His Phe Thr Glu His Tyr Ala Arg Phe Ile Pro Thr Ile
    50                  55                  60

Leu Ser Val Ala Ile Pro Leu Ile Gln Arg Asp Ala Val Gly Leu Phe
65                  70                  75                  80

Gln Val Ala Asn Ala Ser Ile Ala Thr Thr Leu Leu Thr His Thr Thr
                85                  90                  95

Lys Arg Ala Leu Asn His Val Thr Ile Asn Asp Gln Arg Leu Gly Glu
            100                 105                 110

Arg Pro Tyr Gly Gly Asn Phe Asn Met Pro Ser Gly His Ser Ser Met
        115                 120                 125

Val Gly Leu Ala Val Ala Phe Leu Met Arg Arg Tyr Ser Phe Lys Lys
    130                 135                 140

Tyr Phe Trp Leu Leu Pro Leu Val Pro Leu Thr Met Leu Ala Arg Ile
145                 150                 155                 160

Tyr Leu Asp Met His Thr Ile Gly Ala Val Leu Thr Gly Leu Gly Val
                165                 170                 175

Gly Met Leu Cys Val Ser Leu Phe Thr Ser Pro Lys Lys Pro
            180                 185                 190
```

<210> SEQ ID NO 13
<211> LENGTH: 573
<212> TYPE: DNA
<213> ORGANISM: Artificial Sequence
<220> FEATURE:
<223> OTHER INFORMATION: Polynucleodide encoding Helicobactor pylori
      LpxE mutant

<400> SEQUENCE: 13

```
atgaaaaaat tcttatttaa acaaaaattt tgtgaaagcc tgcccaaatc gtttctaaaa    60
actttgttag cgctcagttt gggcttgatt ttattaggca ttttttgcgcc tttccctaaa   120 gtccctaaac agcctagcgt gccttttaatg tttcatttca ccgagcatta tgcgcgcttt   180
atccctacga ttttatctgt ggcgattccc ttaatccaaa gagatgcggt agggcttttt   240
caagtcgcta acgcttctat cgctacaacc cttctcacgc acaccaccaa aagagcctta   300
aaccatgtaa caatcaacga tcagcgtttg ggcgagcgcc cttatggagg taatttcaac   360
atgccaagcg ggcattcgtc tatggtgggt ttggcggtgg cgttttttaat gcgccgctat   420 tcttttaaaa aatactttttg gctcttgccc ctagtccctt tgaccatgct cgctcgcatt   480
tatttagaca tgcacaccat ggcgcgggtg ctgaccgggc ttggcgttgg aatgttgtgc   540
```

```
gtaagccttt ttacaagccc caaaaagcct taa                                      573
```

<210> SEQ ID NO 14
<211> LENGTH: 55
<212> TYPE: DNA
<213> ORGANISM: Artificial Sequence
<220> FEATURE:
<223> OTHER INFORMATION: Forward primer for amplifying HpLpxE mutant

<400> SEQUENCE: 14

```
gatcctctag aaaggagata tattgatgaa aaaattctta tttaaacaaa aattt            55
```

<210> SEQ ID NO 15
<211> LENGTH: 29
<212> TYPE: DNA
<213> ORGANISM: Artificial Sequence
<220> FEATURE:
<223> OTHER INFORMATION: Reverse primer for amplifying Helicobactor
      pylori LpxE mutant

<400> SEQUENCE: 15

```
agctacaagc ttttaaggct ttttggggc                                          29
```

<210> SEQ ID NO 16
<211> LENGTH: 30
<212> TYPE: DNA
<213> ORGANISM: Artificial Sequence
<220> FEATURE:
<223> OTHER INFORMATION: Forward primer for amplifying frt-kan-frt

<400> SEQUENCE: 16

```
gcagaagctt gtgtaggctg gagctgcttc                                         30
```

<210> SEQ ID NO 17
<211> LENGTH: 34
<212> TYPE: DNA
<213> ORGANISM: Artificial Sequence
<220> FEATURE:
<223> OTHER INFORMATION: Reverse primer for amplifying frt-kan-frt

<400> SEQUENCE: 17

```
gcagaagctt atgaatatcc tccttagttc ctat                                    34
```

<210> SEQ ID NO 18
<211> LENGTH: 237
<212> TYPE: PRT
<213> ORGANISM: Artificial Sequence
<220> FEATURE:
<223> OTHER INFORMATION: Escherichia coli LpxT polypeptide

<400> SEQUENCE: 18

```
Met Ile Lys Asn Leu Pro Gln Ile Val Leu Leu Asn Ile Val Gly Leu
1               5                   10                  15

Ala Leu Phe Leu Ser Trp Tyr Ile Pro Val Asn His Gly Phe Trp Leu
            20                  25                  30

Pro Ile Asp Ala Asp Ile Phe Tyr Phe Phe Asn Gln Lys Leu Val Glu
        35                  40                  45

Ser Lys Ala Phe Leu Trp Leu Val Ala Leu Thr Asn Asn Arg Ala Phe
    50                  55                  60

Asp Gly Cys Ser Leu Leu Ala Met Gly Met Leu Met Leu Ser Phe Trp
65                  70                  75                  80

Leu Lys Glu Asn Ala Pro Gly Arg Arg Arg Ile Val Ile Ile Gly Leu
                85                  90                  95
```

Val Met Leu Leu Thr Ala Val Val Leu Asn Gln Leu Gly Gln Ala Leu
            100                 105                 110

Ile Pro Val Lys Arg Ala Ser Pro Thr Leu Thr Phe Thr Asp Ile Asn
            115                 120                 125

Arg Val Ser Glu Leu Leu Ser Val Pro Thr Lys Asp Ala Ser Arg Asp
            130                 135                 140

Ser Phe Pro Gly Asp His Gly Met Met Leu Leu Ile Phe Ser Ala Phe
145                 150                 155                 160

Met Trp Arg Tyr Phe Gly Lys Val Ala Gly Leu Ile Ala Leu Ile Ile
                165                 170                 175

Phe Val Val Phe Ala Phe Pro Arg Val Met Ile Gly Ala His Trp Phe
            180                 185                 190

Thr Asp Ile Ile Val Gly Ser Met Thr Val Ile Leu Ile Gly Leu Pro
            195                 200                 205

Trp Val Leu Leu Thr Pro Leu Ser Asp Arg Leu Ile Thr Phe Phe Asp
            210                 215                 220

Lys Ser Leu Pro Gly Lys Asn Lys His Phe Gln Asn Lys
225                 230                 235

<210> SEQ ID NO 19
<211> LENGTH: 714
<212> TYPE: DNA
<213> ORGANISM: Artificial Sequence
<220> FEATURE:
<223> OTHER INFORMATION: Polynucleotide encoding Escherichia coli LpxT
      polypeptide

<400> SEQUENCE: 19
atgattaaaa atttgccgca aatagtgttg ttgaatattg tcggcctcgc gctgtttctt      60
tcctggtata tccccgttaa tcatggattc tggttgccga ttgatgcgga tattttttat     120
ttctttaatc agaaactggt cgaaagtaag gccttttttgt ggctggttgc attgaccaac    180
aatcgcgcct tcgacggttg ttcactgctg gcgatgggta tgttgatgct gagtttctgg     240
ctgaaagaaa acgcccctgg cagacgacgt atcgtgatta ttggtctggt catgctatta     300
actgcagtgg tattaaacca gctgggtcag gcattaattc ctgtaaaacg gccagcccca    360
acattgactt ttaccgatat taaccgcgtc agcgaactgc tctctgttcc cacgaaagat     420
gcctcacgag atagctttcc cggcgatcac ggcatgatgc tgcttatttt ttcggcattc     480
atgtggcgtt atttcggcaa agttgcaggc cttatcgccc ttattatttt tgtggttttt     540
gcatttccca gagtaatgat tggcgcacac tggtttactg acatcattgt cggttcgatg     600
accgtgatat tgatcggttt gccctgggtg ttgctgacgc cattaagtga tcgattaatc    660
acctttttgt acaaatcact accaggaaaa aacaaacatt tccaaaacaa ataa          714

<210> SEQ ID NO 20
<211> LENGTH: 89
<212> TYPE: DNA
<213> ORGANISM: Artificial Sequence
<220> FEATURE:
<223> OTHER INFORMATION: Forward primer amplifying
      bacA::HpLpxE-frt-kan-frt

<400> SEQUENCE: 20
aacctggtca tacgcagtag ttcggacaag cggtacattt taataattta ggggtttatt     60
gatgaaaaaa ttcttattta aacaaaaat                                      89

<210> SEQ ID NO 21

<211> LENGTH: 89
<212> TYPE: DNA
<213> ORGANISM: Artificial Sequence
<220> FEATURE:
<223> OTHER INFORMATION: Reverse primer amplifying
    bacA::HpLpxE-frt-kan-frt

<400> SEQUENCE: 21
tgacaacgcc aagcatccga cactattcct caattaaaag aacacgacat acaccgcagc    60
cgccacatga atatcctcct tagttccta                                      89

<210> SEQ ID NO 22
<211> LENGTH: 425
<212> TYPE: PRT
<213> ORGANISM: Artificial Sequence
<220> FEATURE:
<223> OTHER INFORMATION: Escherichia coli KdtA polypeptide

<400> SEQUENCE: 22

Met Leu Glu Leu Leu Tyr Thr Ala Leu Leu Tyr Leu Ile Gln Pro Leu
1               5                   10                  15

Ile Trp Ile Arg Leu Trp Val Arg Gly Arg Lys Ala Pro Ala Tyr Arg
            20                  25                  30

Lys Arg Trp Gly Glu Arg Tyr Gly Phe Tyr Arg His Pro Leu Lys Pro
        35                  40                  45

Gly Gly Ile Met Leu His Ser Val Ser Val Gly Glu Thr Leu Ala Ala
    50                  55                  60

Ile Pro Leu Val Arg Ala Leu Arg His Arg Tyr Pro Asp Leu Pro Ile
65                  70                  75                  80

Thr Val Thr Thr Met Thr Pro Thr Gly Ser Glu Arg Val Gln Ser Ala
                85                  90                  95

Phe Gly Lys Asp Val Gln His Val Tyr Leu Pro Tyr Asp Leu Pro Asp
            100                 105                 110

Ala Leu Asn Arg Phe Leu Asn Lys Val Asp Pro Lys Leu Val Leu Ile
        115                 120                 125

Met Glu Thr Glu Leu Trp Pro Asn Leu Ile Ala Ala Leu His Lys Arg
    130                 135                 140

Lys Ile Pro Leu Val Ile Ala Asn Ala Arg Leu Ser Ala Arg Ser Ala
145                 150                 155                 160

Ala Gly Tyr Ala Lys Leu Gly Lys Phe Val Arg Arg Leu Leu Arg Arg
                165                 170                 175

Ile Thr Leu Ile Ala Ala Gln Asn Glu Glu Asp Gly Ala Arg Phe Val
            180                 185                 190

Ala Leu Gly Ala Lys Asn Asn Gln Val Thr Val Thr Gly Ser Leu Lys
        195                 200                 205

Phe Asp Ile Ser Val Thr Pro Gln Leu Ala Ala Lys Ala Val Thr Leu
    210                 215                 220

Arg Arg Gln Trp Ala Pro His Arg Pro Val Trp Ile Ala Thr Ser Thr
225                 230                 235                 240

His Glu Gly Glu Glu Ser Val Val Ile Ala Ala His Gln Ala Leu Leu
                245                 250                 255

Gln Gln Phe Pro Asn Leu Leu Leu Ile Leu Val Pro Arg His Pro Glu
            260                 265                 270

Arg Phe Pro Asp Ala Ile Asn Leu Val Arg Gln Ala Gly Leu Ser Tyr
        275                 280                 285

Ile Thr Arg Ser Ser Gly Glu Val Pro Ser Thr Ser Thr Gln Val Val
    290                 295                 300

Val Gly Asp Thr Met Gly Glu Leu Met Leu Leu Tyr Gly Ile Ala Asp
305                 310                 315                 320

Leu Ala Phe Val Gly Gly Ser Leu Val Glu Arg Gly Gly His Asn Pro
            325                 330                 335

Leu Glu Ala Ala Ala His Ala Ile Pro Val Leu Met Gly Pro His Thr
        340                 345                 350

Phe Asn Phe Lys Asp Ile Cys Ala Arg Leu Glu Gln Ala Ser Gly Leu
    355                 360                 365

Ile Thr Val Thr Asp Ala Thr Thr Leu Ala Lys Glu Val Ser Ser Leu
370                 375                 380

Leu Thr Asp Ala Asp Tyr Arg Ser Phe Tyr Gly Arg His Ala Val Glu
385                 390                 395                 400

Val Leu Tyr Gln Asn Gln Gly Ala Leu Gln Arg Leu Leu Gln Leu Leu
                405                 410                 415

Glu Pro Tyr Leu Pro Pro Lys Thr His
            420                 425

<210> SEQ ID NO 23
<211> LENGTH: 1278
<212> TYPE: DNA
<213> ORGANISM: Artificial Sequence
<220> FEATURE:
<223> OTHER INFORMATION: Polynucleotide encoding Escherichia coli KdtA
      polypeptide

<400> SEQUENCE: 23
atgctcgaat tgctttacac cgcccttctc taccttattc agccgctgat ctggatacgg      60
ctctgggtgc gcggacgtaa ggctccggcc tatcgaaaac gctggggtga acgttacggt     120
ttttaccgcc atccgctaaa accaggcggc attatgctgc actccgtctc cgtcggtgaa     180
actctggcgg caatcccgtt ggtgcgcgcg ctgcgtcatc gttatcctga tttaccgatt     240
accgtaacaa ccatgacgcc aaccggttcg gagcgcgtac aatcggcttt cgggaaggat     300
gttcagcacg tttatctgcc gtatgatctg cccgatgcac tcaaccgttt cctgaataaa     360
gtcgacccta aactggtgtt gattatggaa accgaactat ggcctaacct gattgcggcg     420
ctacataaac gtaaaattcc gctggtgatc gctaacgcgc gactctctgc ccgctcggcc     480
gcaggttatg ccaaactggg taaattcgtc cgtcgcttgc tgcgtcgtat tacgctgatt     540
gctgcgcaaa atgaagaaga tggtgcacgt tttgtggcgc tgggcgcaaa aaataatcag     600
gtgaccgtta ccggtagcct gaaattcgat atttctgtaa cgccgcagtt ggctgctaaa     660
gccgtgacgc tgcgccgcca gtgggcacca caccgcccgg tatggattgc caccagcact     720
cacgaaggcg aagagagtgt ggtgatcgcc gcacatcagg cattgttaca gcaattcccg     780
aatttattgc tcatcctggt accccgtcat ccggaacgct cccggatgc gattaacctt     840 gtccgccagg ctggactaag ctatatcaca cgctcttcag gggaagtccc ctccaccagc     900
acgcaggttg tggttggcga tacgatgggc gagttgatgt tactgtatgg cattgccgat     960
ctcgcctttg ttggcggttc actggttgaa cgtggtgggc ataatccgct ggaagctgcc    1020
gcacacgcta ttccggtatt gatggggccg catacttttta actttaaaga catttgcgcg    1080
cggctggagc aggcaagcgg gctgattacc gttaccgatg ccactacgct tgcaaaagag    1140
gtttcctctt tactcaccga cgccgattac cgtagtttct atggccgtca tgccgttgaa    1200
gtactgtatc aaaaccaggg cgcgctacag cgtctgcttc aactgctgga accttacctg    1260
ccaccgaaaa cgcattga                                                  1278

```
<210> SEQ ID NO 24
<211> LENGTH: 80
<212> TYPE: DNA
<213> ORGANISM: Artificial Sequence
<220> FEATURE:
<223> OTHER INFORMATION: Forward primer amplifying kdtA::frt-kan-frt

<400> SEQUENCE: 24
gctaaataca tagaatcccc agcacatcca taagtcagct atttactatg ctcgaattgc    60
gtgtaggctg gagctgcttc                                                80

<210> SEQ ID NO 25
<211> LENGTH: 86
<212> TYPE: DNA
<213> ORGANISM: Artificial Sequence
<220> FEATURE:
<223> OTHER INFORMATION: Reverse primer amplifying kdtA::frt-kan-frt

<400> SEQUENCE: 25
atcgatatga ccattggtaa tgggatcgaa agtacccgga taaatcgccc gttttttgcat   60 tgaatatcct ccttagttcc tattcc                                          86
```

BACTERIUM CONSTITUTIVELY PRODUCING MONOPHOSPHORYL LIPID A AND METHOD OF PRODUCING MONOPHOSPHORYL LIPID A BY USING BACTERIUM

CROSS-REFERENCE TO RELATED APPLICATION

This application claims the benefit of Korean Patent Application No. 10-2017-0085406, filed on Jul. 5, 2017, in the Korean Intellectual Property Office, the disclosure of which is incorporated herein in its entirety by reference.

BACKGROUND

1. Field

One or more embodiments relate to a bacterium that constitutively produces monophosphoryl lipid A (MLA), and a method of producing MLA by using the bacterium.

2. Description of the Related Art

Lipopolysaccharides (LPS) are one of the components of the outer membrane which surrounds peptidoglycan in Gram-negative bacteria. LPS are molecules containing lipid A and a variety of polysaccharides conjugated with the lipid A by a covalent bond. Among the components of LPS, Lipid A, which is also known as endotoxin, is held responsible for the toxicity of Gram-negative bacteria.

Lipid A is a very potent stimulant of the immune system, activating cells (for example, monocytes or macrophages) at picogram per milliliter quantities. Derivatives of lipid A or variants of lipid A can be used as, for example, components of vaccines such as adjuvants. Monophosphoryl lipid A (MLA) is used as an adjuvant and used for allergen-specific immunotherapy and immunotherapy for cancer, and has also been reported to be effective in the prevention and treatment of dementia. Lipid A found in the membrane of Gram-negative bacteria, such as *Escherichia coli*, conjugates with sugars such as 2-keto-3-deoxy-D-manno-octulosonate (Kdo). Accordingly, MLA may be produced by extracting LPS from the outer membrane of bacteria, heating LPS in the presence of an acid, and hydrolyzing LPS in the presence of sodium carbonate to remove Kdo and a 1-phosphate group or an acyl chain, or by a chemical synthesis method. However, these methods involve complicated processes and produce low yields.

When introducing foreign genes into bacteria by using a genetic engineering method, the bacteria may eliminate the foreign gene by natural mutagenesis to inhibit expression of the foreign gene. Such natural mutagenesis may cause a reduction in genetic engineering transformation efficiency and stability of the genetic engineering.

Therefore, there is a need to develop a method of producing MLA and derivatives thereof that is simpler than methods of the related art, does not involve acid hydrolysis, reduces the probability of natural mutagenesis that reduces MLA production, and results in constitutive expression of MLA and derivatives thereof such that yield is increased.

SUMMARY

One or more embodiments include a bacterium that constitutively produces monophosphoryl lipid A (MLA).

One or more embodiments include a method of producing MLA with a high yield.

Additional aspects will be set forth in part in the description which follows and, in part, will be apparent from the description, or may be learned by practice of the presented embodiments.

According to one or more embodiments, there is provided a bacterium that constitutively produces monophosphoryl lipid A (MLA), wherein the bacterium includes an LpxE polypeptide, and a chromosome of the bacterium includes a mutation in a polynucleotide that encodes an undecaprenyl pyrophosphate phosphatase (Und-PP phosphatase), a polynucleotide that encodes a phosphatidylglycerophosphate phosphatase (PGP phosphatase), or a combination thereof.

According to one or more embodiments, a method of producing monophosphoryl lipid A (MLA) includes: culturing the bacterium according to any of the above-described embodiments to obtain a culture; collecting the bacterium from the culture; and isolating MLA from the collected bacterium.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
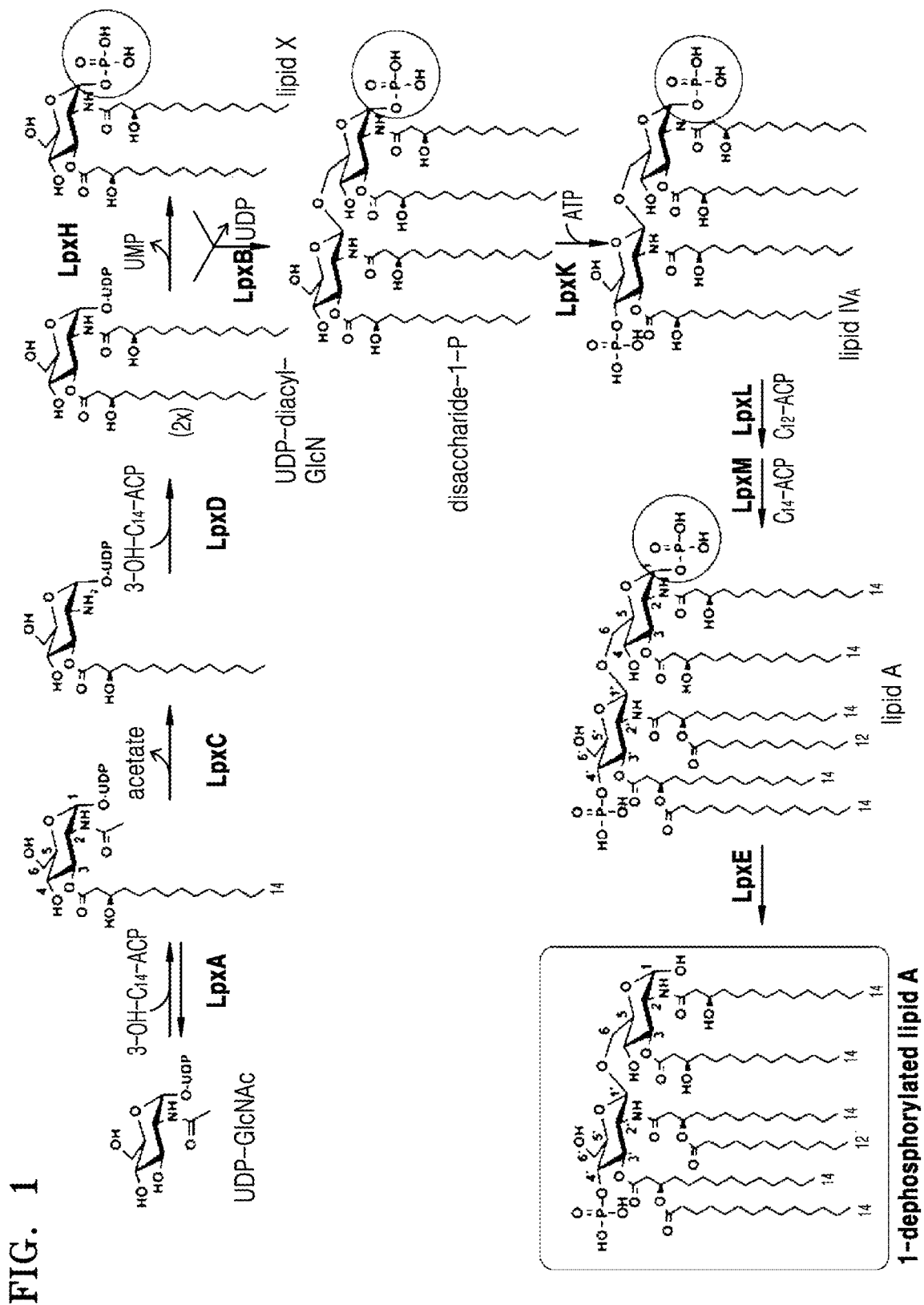
FIG. 1 is a schematic view illustrating a process of producing 1-dephospho-lipid A in a bacterium according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The term "increase expression" used herein refers to a detectable increase in expression product of a certain gene, for example, mRNA or a protein encoded by the gene in a cell. The term "parent bacterial cell" used herein refers to a bacterial cell of the same type that does not have a particular genetic modification. When a wild-type cell is used in the genetic modification, the parent bacterial cell may be a "wild-type" cell. For example, bacterium comprising a genetic modification that increases expression of a gene may have higher level of expression product than that of parent bacterial cell by about 5% or more, about 10% or more, about 15% or more, about 20% or more, about 30% or more, about 40% or more, about 50% or more, about 60% or more, about 70% or more, about 80% or more, about 90% or more, about 95% or more, or about 100% or more. Increase in expression product in a cell may be verified by any methods known in the art. The level of expression product may be determined by measuring activities or quantities of the expression product such as mRNA or protein.

Genetic modification includes a modification that introduces a polynucleotide encoding a polypeptide into a cell; a modification that substitutes, adds (i.e., inserts), or deletes one or more nucleotides of the genetic material of a parent cell, including a chemical modification (exposure to a chemical) resulting in a change to the genetic material of a parent cell. Genetic modification includes a heterologous or homologous modification of referenced species. Genetic modification includes a modification of a coding region for polypeptides. Genetic modification also includes a modification of non-coding regulatory regions that change expression of a gene or function of an operon. Non-coding regions include 5'-non-coding sequence (5' of a coding sequence) and 3'-non-coding sequence (3' of a coding sequence).

The term "sequence identity" of a nucleic acid or polypeptide used herein refers to a degree of identity of nucleotides or amino acid residues of two corresponding sequences over a particular region measured after the sequences are aligned to be matched with each other as much as possible. The sequence identity is a value that is measured by comparing two optimally aligned corresponding sequences of a particular comparable region, wherein in the comparable region, a part of the sequence may be added or deleted compared to a reference sequence. In some embodiments, a percentage of the sequence identity may be calculated by comparing two optimally aligned corresponding sequences in an entire comparable region, determining the number of locations where an amino acid or a nucleic acid is identical in the two sequences to obtain the number of matched locations, dividing the number of the matched locations by the total number (that is, a range size) of all locations within a comparable range, and multiplying the result by 100 to obtain a percentage of the sequence identity. The percent of the sequence identity may be determined by using known sequence comparison programs, examples of which include BLASTN and BLASTP (NCBI), CLC Main Workbench (CLC bio.), MegAlign™ (DNASTAR Inc).

In identifying polypeptides or polynucleotides of different species that may have identical or similar function or activity, similarity in sequence identity may be used. For example, similar sequences may have a sequence identity of 50% or more, 55% or more, 60% or more, 65% or more, 70% or more, 75% or more, 80% or more, 85% or more, 90% or more, 95% or more, 96% or more, 97% or more, 98% or more, 99% or more, or 100%.

The term "exogenous" and the like used herein refers to a referenced molecule (e.g., nucleic acid) or referenced activity that has been introduced into a host cell. A nucleic acid may be exogenously introduced into a host in any suitable manner. For example, a nucleic acid can be introduced into a host cell and inserted into a host chromosome, or the nucleic acid can be introduced into the host as non-chromosomal genetic material, such as an expression vector (e.g., a plasmid) that does not integrate into the host chromosome. A nucleic acid encoding a protein should be introduced in an expressionable form (i.e., so that the nucleic acid can be transcribed and translated). The exogenous gene may include a homologous gene, i.e., an identical gene with the endogenous gene, or a heterologous gene.

An aspect provides a bacterium that constitutively produces monophosphoryl lipid A (MLA).

The bacterium may include a genetic modification that increases expression of a gene encoding LpxE polypeptide as compared to a parent bacterial cell. A chromosome of the bacterium may include a mutation of a polynucleotide that encodes an undecaprenyl pyrophosphate phosphatase (Und-PP phosphatase), a mutation of a polynucleotide that encodes a phosphatidylglycerophosphate phosphatase (PGP phosphatase), or a combination thereof.

Lipid A moiety in monophosphoryl lipid A consists of two glucosamines (carbohydrates or sugars) with attached acyl chains, and normally contains one phosphate group in each glucosamine. Two disaccharides may linked by $\beta(1\rightarrow6)$ linkage. The acyl chain may be directly attached to hydroxyl residue selected from the group of hydroxyl residue at C-2, C-2', C-3 and C-3' positions of glucosamine disaccharide. The acyl chain may have hydroxyl residue, for example at C-3 position thereof and additional acyl chain may be attached to hydroxyl residue located in the acyl chain. Each of the acyl chain attached may have identical or different. Depending on the number of acyl chains, lipid A may be tri-acylated lipid A, tetra-acylated lipid A, penta-acylated lipid A, or hexa-acylated lipid A, hepa-acylated lipid A. Lipid A that effectively activates an immune system is known to contain six acyl chains. Four acyl chains attached directly to the glucosamines may be beta hydroxy acyl chains consisting of 10 to 22 carbons, and two additional acyl chains are mostly attached to a beta hydroxy group.

The MLA refers to a monophosphoryl lipid A in which only one phosphate group is joined to C-1 or C-4' position of glucosamine disaccharide. The MLA may be tri-acylated MLA, tetra-acylated MLA, penta-acylated MLA, hexa-acylated MLA, or hepta-acylated MLA. For example, the MLA may be 1-dephospho-lipid A, 1-dephospho-tetra-acylated lipid A, 1-dephospho-penta-acylated lipid A, or a combination thereof.

The MLA may not include 2-keto-3-deoxy-D-mannooctulosonate (Kdo). Kdo is a component of lipopolysaccharides (LPS) conserved in almost all LPS.

The MLA may be present in a membrane, for example, in an outer membrane, of a living bacterium.

The term "bacterium" as used herein refers to a prokaryotic bacterium. The bacterium may be a Gram-negative bacterium. Gram-negative bacteria refer to a type of bacteria that does not stain with crystal violet used in a Gram staining method. The cell membranes of Gram-negative bacteria consist of a double membrane including an inner membrane and an outer membrane, and include a thin peptidoglycan layer. The bacterium may be selected from the group consisting of *Escherichia* genus bacteria, *Shigella* genus bacteria, *Salmonella* genus bacteria, *Campylobacter* genus bacteria, *Neisseria* genus bacteria, *Haemophilus* genus bacteria, *Aeromonas* genus bacteria, *Francisella* genus bacteria, *Yersinia* genus bacteria, *Klebsiella* genus bacteria, *Bordetella* genus bacteria, *Legionella* genus bacteria, *Corynebacteria* genus bacteria, *Citrobacter* genus bacteria, *Chlamydia* genus bacteria, *Brucella* genus bacteria, *Pseudomonas* genus bacteria, *Helicobacter* genus bacteria, *Burkholderia* genus bacteria, *Porphyromonas* genus bacteria, *Rhizobium* genus bacteria, *Mesorhizobium* genus bacteria, and *Vibrio* genus bacteria. For example, the bacterium may be *Escherichia coli*.

The bacterium according to one or more embodiments may constitutively produce MLA. The term "constitutively" as used herein may refer to production that occurs irrespective of the presence of an expression inducer, an expression-inducing stimulus, or antibiotics.

The bacterium according to one or more embodiments may include increased copy number of gene encoding LpxE polypeptide. The bacterium may include at least one of an exogenous polynucleotide encoding LpxE polypeptide.

The LpxE polypeptide belongs to EC 3.1.3.-. The LpxE belongs to the family of lipid phosphate phosphatases. The LpxE may contain a tripartite active site and six transmembrane helices. A lipid phosphate phosphatase is a hydrolase, specifically acting to phosphoric monoester bonds, which may remove a phosphate group from a lipid containing a phosphate group. The LpxE may be phosphate phosphatase specifically dephosphorylating the 1-position. The LpxE polypeptide may be an LpxE polypeptide of bacterium selected from the group consisting of *Aquifex* genus bacterium, *Helicobacter* genus bacterium, *Francisella* genus bacterium, *Bordetella* genus bacterium, *Brucella* genus bacterium, *Rhizobium* genus bacterium, *Mesorhizobium* genus bacterium, *Legionella* genus bacterium, *Agrobacterium* genus bacterium, *Chlorobium* genus bacterium, *Rhodospirillum* genus bacterium, *Magnetospirillum* genus bacterium, *Chlorobaculum* genus bacterium, *Pelodictyon* genus bacterium, *Pseudovibro* genus bacterium, *Phaeospirillum* genus bacterium, *Syntrophobacter* genus bacterium, *Bradyrhizobium* genus bacterium, *Porphyromonas* genus bacterium, *Ralstonia* genus bacterium, *Limnohabitans* genus bacterium, and *Thermodesulfobacterium* genus bacterium. The *Aquifex* genus bacterium may include *Aquifex aeolicus* or *Aquifex pyrophilus*. *Aquifex* genus bacterium is thermophilic bacterium, which may grow best at a temperature ranging from about 85° C. to 95° C. The *Aquifex* genus bacterium may be *Aquifex aeolicus*. The *Helicobacter* genus bacterium may be *Helicobacter pylori*. For example, the LpxE polypeptide may be an LpxE polypeptide derived from *Aquifex aeolicus* (AaLpxE) or an LpxE polypeptide derived from *Helicobacter pylori* (HμLpxE). The LpxE polypeptide may be a polypeptide that includes an amino acid sequence of SEQ ID NO: 12; or a polypeptide having a sequence identity of about 99%, about 97%, about 95%, about 90%, about 80%, about 70%, about 60%, about 50%, about 40%, about 30%, about 20%, about 10% or more to the amino acid sequence of SEQ ID NO:12. The LpxE polypeptide may be a mutated polypeptide.

A polynucleotide that encodes the LpxE polypeptide may be in a chromosome of the bacterium. The polynucleotide that encodes the LpxE polypeptide may be a polypeptide including an amino acid sequence having a sequence identity of about 90 about 99%, about 97%, about 95%, about 80%, about 70%, about 60%, about 50%, about 40%, about 30%, about 20%, about 10% or more to a nucleic acid sequence of SEQ ID NO: 13. The polynucleotide may be a mutated nucleotide sequence. For example, the polynucleotide may include a genetic mutation of a nucleotide sequence that encodes the 17th amino acid serine (17Ser) from the N-terminal of a wild-type LpxE polypeptide, from AGC to TCG.

The polynucleotide that encodes the LpxE polypeptide may be constitutively expressed. The expression "constitutively expressed" may refer to expression of a gene without an expression inducer or an expression inducing stimulus.

The bacterium according to one or more embodiments may include, in a chromosome of the bacterium, a mutation in a polynucleotide that encodes a undecaprenyl pyrophosphate phosphatase (Und-PP phosphatase), a polynucleotide that encodes a phosphatidylglycerophosphate phosphatase (PGP phosphatase), or a combination thereof. The term "bacterial chromosome", which contains genetic information of the bacterium, may be circular DNA. The bacterium chromosome may be plasmid-free. A plasmid refers to circular DNA that is physically separate from a bacterial chromosome and can replicate independently.

The Und-PP phosphatase is an enzyme that produces an undecaprenyl phosphate by catalyzing dephosphorylation of an undecaprenyl pyrophosphate. An undecaprenyl phosphate is a lipid carrier of a glycan biosynthetic intermediate for a hydrocarbon polymer that is transmitted to the envelope of bacteria.

The polynucleotide that encodes the Und-PP phosphatase may be a bacA gene, a pgpB gene, a ybjG gene, or a combination thereof. The bacA gene is a gene of which overexpression confers resistance to a known antibiotic, bacitracin. The pgpB gene is a gene that encodes an enzyme catalyzing dephosphorylation of phosphatidylglycerol phosphate (PGP) to generate phosphatidyl glycerol (PG). This enzyme may have the activity of Und-PP phosphatase. The ybjG gene is a gene of which overexpression increases the activity of Und-PP phosphatase and increases resistance to bacitracin.

The polynucleotide that encodes the PGP phosphatase may be a pgpB gene, a pgpA gene, a pgpC gene, or a combination thereof. The pgpA gene or pgpC gene is a gene encoding a lipid phosphatase that dephosphorylates PGP to PG.

For example, the bacterium may include a mutation in a bacA gene, a mutation in a pgpB gene, and a mutation in a ybjG gene.

The term "gene", which is a unit of genetic information, may include an open reading frame (ORF) encoding a polypeptide, and a regulatory sequence regulating transcription of the gene. The regulatory sequence may include a promoter that is a DNA domain initiating transcription of a gene, an enhancer promoting transcription, a silencer that may inhibit transcription, or a combination thereof.

The term "mutation" refers to a modification of genetic material, and may include a point mutation, a frameshift mutation, an insertion, a deletion, an inversion, or a translocation. For example, the mutation may be a deletion, an insertion, a point mutation, a frameshift mutation, or a combination thereof. The point mutation may be a missense mutation or a nonsense mutation. By a mutation, genetic material may be deleted from or introduced into the genome of the bacterium.

The bacterium according to one or more embodiments may further include a polynucleotide encoding a polypeptide selected from the group consisting of a LpxL polypeptide and a LpxM polypeptide. The polynucleotide may be inducible or constitutively expressed. The inducible expression may refer to expression by an expression inducer or an expression inducing stimulus (for example, thermal treatment. The constitutive expression may refer to expression without an expression inducer or an expression inducing stimulus. The polynucleotide may be expressed by a promoter selected from the group consisting of a $P_L$ promoter, a $P_R$ promoter, and a $P_{R'}$ promoter. The $P_L$ promoter, the $P_R$ promoter, and the $P_{R'}$ promoter may be promoters derived from Lambda phage.

The LpxL polypeptide may belong to EC 2.3.1.241. The LpxL polypeptide is a lipid A biosynthesis lauroyltransferase, which catalyzes the transfer of laurate from a lauroyl-acyl carrier protein (ACP) to $Kdo_2$-lipid IVa to synthesize a $Kdo_2$-(lauroyl)-lipid IVa. The LpxL polypeptide may be an LpxL polypeptide of a bacterium selected from the group consisting of an *Escherichia* genus bacterium, a *Shigella* genus bacterium, a *Salmonella* genus bacterium, a *Campylobacter* genus bacterium, a *Neisseria* genus bacterium, a *Haemophilus* genus bacterium, an *Aeromonas* genus bacterium, a *Francisella* genus bacterium, a *Yersinia* genus bacterium, a *Klebsiella* genus bacterium, a *Bordetella* genus bacterium, a *Legionella* genus bacterium, a *Corynebacterium* genus bacterium, a *Citrobacter* genus bacterium, a *Chlamydia* genus bacterium, a *Brucella* genus bacterium, a *Pseudomonas* genus bacterium, a *Helicobacter* genus bacterium, a *Burkholderia* genus bacterium, a *Porphyromonas* genus bacterium, a *Rhizobium* genus bacterium, a *Mesorhizobium* genus bacterium, and a *Vibrio* genus bacterium. For example, the LpxL polypeptide may be an LpxL polypeptide of *Escherichia coli* (EcLpxL). The LpxL polypeptide may be a polypeptide that includes an amino acid sequence of SEQ ID NO: 1; or a polypeptide having a sequence identity of about 99%, about 97%, about 95%, about 90%, about 80%, about 70%, about 60%, about 50%, about 40%, about 30%, about 20%, about 10% or more to the amino acid sequence of SEQ ID NO: 1. The LpxL polypeptide may be encoded by a nucleic acid sequence of SEQ ID NO: 2; or by a polynucleotide having a sequence identity of about 90%, about 80%, about 70%, about 60%, about 50%, about 40%, about 30%, about 20%, about 10% or more to the nucleic acid sequence of SEQ ID NO: 2.

The LpxM polypeptide may belong to EC 2.3.1.243. The LpxM polypeptide is a lipid A biosynthesis myristoyltransferase, which catalyzes the transfer of myristate from a myristoyl-acyl carrier protein to $Kdo_2$-lauroyl-lipid $IV_A$ to synthesize $Kdo_2$-lipid A. The LpxM polypeptide may be an LpxM polypeptide of a bacterium selected from the group consisting of an *Escherichia* genus bacterium, a *Shigella* genus bacterium, a *Salmonella* genus bacterium, a *Campylobacter* genus bacterium, a *Neisseria* genus bacterium, a *Haemophilus* genus bacterium, an *Aeromonas* genus bacterium, a *Francisella* genus bacterium, a *Yersinia* genus bacterium, a *Klebsiella* genus bacterium, a *Bordetella* genus bacterium, a *Legionella* genus bacterium, a *Corynebacterium* genus bacterium, a *Citrobacter* genus bacterium, a *Chlamydia* genus bacterium, a *Brucella* genus bacterium, a *Pseudomonas* genus bacterium, a *Helicobacter* genus bacterium, a *Burkholderia* genus bacterium, a *Porphyromonas* genus bacterium, a *Rhizobium* genus bacterium, a *Mesorhizobium* genus bacterium, and a *Vibrio* genus bacterium. For example, the LpxM polypeptide may be an LpxM polypeptide of *Escherichia coli* (EcLpxM). The LpxM polypeptide may be a polypeptide that includes an amino acid sequence of SEQ ID NO: 5; or a polypeptide having a sequence identity of about 99%, about 97%, about 95%, about 90%, about 80%, about 70%, about 60%, about 50%, about 40%, about 30%, about 20%, about 10% or more to the amino acid sequence of SEQ ID NO: 5. The LpxM polypeptide may be encoded by a nucleic acid sequence of SEQ ID NO: 6; or by a polynucleotide having a sequence identity of about 99%, about 97%, about 95%, about 90%, about 80%, about 70%, about 60%, about 50%, about 40%, about 30%, about 20%, about 10% or more to the nucleic acid sequence of SEQ ID NO: 6.

The bacterium according to one or more embodiments may further include a genetic modification in a polynucleotide that encodes an LpxT polypeptide, a polynucleotide that encodes a PagP polypeptide, a polynucleotide that encodes a KdtA polypeptide, or a combination thereof. The LpxT polypeptide may belong to EC 2.7.4.29. The LpxT polypeptide may be an inner membrane protein LpxT. The LpxT polypeptide may be a polypeptide that includes an amino acid sequence of SEQ ID. NO: 18, or an amino acid sequence having a sequence identity of about 99%, about 97%, about 95%, about 90%, about 80%, about 70%, about 60%, about 50%, about 40%, about 30%, about 20%, about 10% or more to the amino acid sequence of SEQ ID NO: 18. For example, the LpxT polypeptide may be an LpxT polypeptide of *Escherichia coli* (EcLpxT). The PagP polypeptide may belong to EC 2.1.1.251. The PagP polypeptide may be a lipid A palmitoyltransferase required for biosynthesis of a hepta-acylated lipid A species containing palmitate. The KdtA polypeptide may belong to EC 2.4.99.12 2.4.99.13 2.4.99.14 2.4.99.15. The KdtA polypeptide is an enzyme that binds Kdo to lipid $IV_A$. The KdtA polypeptide may be a polypeptide that includes an amino acid sequence of SEQ ID. NO: 22, or an amino acid sequence having a sequence identity of about 99%, about 97%, about 95%, about 90%, about 80%, about 70%, about 60%, about 50%, about 40%, about 30%, about 20%, or about 10% or more to the amino acid sequence of SEQ ID NO: 22. The KdtA polypeptide may be a KdtA polypeptide of *E. coli*.

The bacterium according to one or more embodiments may produce monophosphoryl lipid A (MLA) without induction of expression by an expression inducer, an expression inducing stimulus, or a combination thereof. The expression inducer may be a compound that induces expression of a gene. For example, the expression inducer may be isopropyl β-D-1-thiogalactopyranoside (IPTG), arabinose, tetracycline, tryptophan, or a combination thereof. The expression inducing stimulus, which is a physical stimulus inducing expression of a gene, may be, for example, heat treatment or heat shock.

The bacterium may be cultured without an antibiotic. The antibiotic may be, for example, kanamycin, ampicillin, chloramphenicol, tetracycline, streptomycin, or a combination thereof.

Another aspect provides a method of producing MLA, the method including: culturing the bacterium according to any of the above-described embodiments to obtain a culture; collecting the bacterium from the culture; and isolating MLA from the bacterium.

In regard to the method according to one or more embodiments, the terms "MLA", "constitutively", and "bacterium" used herein below may be the same as defined above.

The method according to one or more embodiments may include culturing the bacterium according to any of the above-described above that constitutively produces MLA.

The culturing may be performed using a known method. For example, the culturing method may be batch culture, fed-batch culture, continuous culture, fermentation, or a combination thereof.

A type of culture medium, a culturing temperature, and culturing conditions may be the same as those known in the art. The culturing temperature may be for example, about 10° C. to about 43° C., about 20° C. to about 43° C., about 20° C. to about 40° C., about 25° C. to about 43° C., about 25° C. to about 35° C., about 27° C. to about 33° C., about 10° C. to about 15° C., about 15° C. to about 20° C., about 20° C. to about 25° C., about 25° C. to about 30° C., about 30° C. to about 33° C., about 33° C. to about 37° C., about 37° C. to about 40° C., or about 40° C. to about 43° C. The bacterium may be cultured in a batch, fed-batch culture, or continuous mode. The culturing may be performed in stationary or shaking condition. The culturing period may be, for example, about 1 hour to about 1 week, about 3 hours to about 6 days, about 6 hours to about 5 days, about 9 hours to about 4 days, about 12 hours to about 3 days, about 18 hours to about 2 days, about 1 day, or overnight. The culture medium may include or may not include an antibiotic. The antibiotic may be, for example, kanamycin, ampicillin, chloramphenicol, tetracycline, streptomycin, or a combination thereof.

The culturing of the bacterium may be performed without an expression inducer, an expression-inducing stimulus, or a combination thereof.

The method according to one or more embodiments may include collecting the bacterium from the culture. The collecting of the bacterium from the culture may be performed using a known method. For example, the collecting of the bacterium may be performed by centrifugation. The collected bacterium may be washed with a buffer solution.

The method according to one or more embodiments may include isolating MLA from the collected bacterium.

The MLA may be separated from lipids of the bacterium. The lipids may be obtained using a method known in the art. The MLA may be obtained using a physical or chemical method. The physical method may be repeatedly using ultrasound pulses or freezing-thawing. The chemical method may be extraction using an organic solvent or precipitation. For example, the organic solvent may include chloroform, phenol, petroleum ether, dichloromethane, methanol, hexane, isopropyl alcohol, ethyl acetate, acetonitrile, ethanol, butanol, or a combination thereof. For example, the method of extraction of the lipids may be a Bligh and Dyer lipid extraction protocol (see Bligh, E. G. and Dyer, W. J., Can. J. Biochem. Physiol., 1959, vol. 37, p. 911-917). The method may further include purifying MLA from the lipids. The method may not include hydrolysis step to remove Kdo moiety since the obtained lipid A may be a free form, i.e., not conjugated to Kdo moiety.

One or more embodiments of the present disclosure will now be described in detail with reference to the following examples. However, these examples are only for illustrative purposes and are not intended to limit the scope of the one or more embodiments of the present disclosure.

Example 1. Preparation of Vector Including Polynucleotide that Encodes *Escherichia coli* LpxL and *Escherichia coli* LpxM 1.1. Preparation of pWSK29-EcLpxLEcLpxM To obtain a polynucleotide that encodes *E. coli* LpxL polypeptides, from the *E. coli* W3110 genome (GenBank Accession No. NC_000918.1, ATCC), a polynucleotide (GenBank Accession No. AP009048.1 (c1118159.1117239, SEQ ID NO: 2), which encodes an EcLpxL polypeptide (GenBank Accession No. BAA35852.1, SEQ ID NO: 1) including a ribosome binding site (RBS), was amplified by a first polymerase chain reaction (PCR) using a pair of primers:

LpxL forward primer P1:
(SEQ ID NO: 3)
5'-CGCAGTCTAGAAAGGAGATATATTGATGACGAATCTACCCAAG
TTCTC-3'

LpxL reverse primer P2:
(SEQ ID NO: 4)
5'-CGCTATTATTTTTTTTCGTTTCCATTGGTATATCTCCTTCTTA
TTAATAGCGTGAAGGAACGCCTTC-3'

Figure 2:
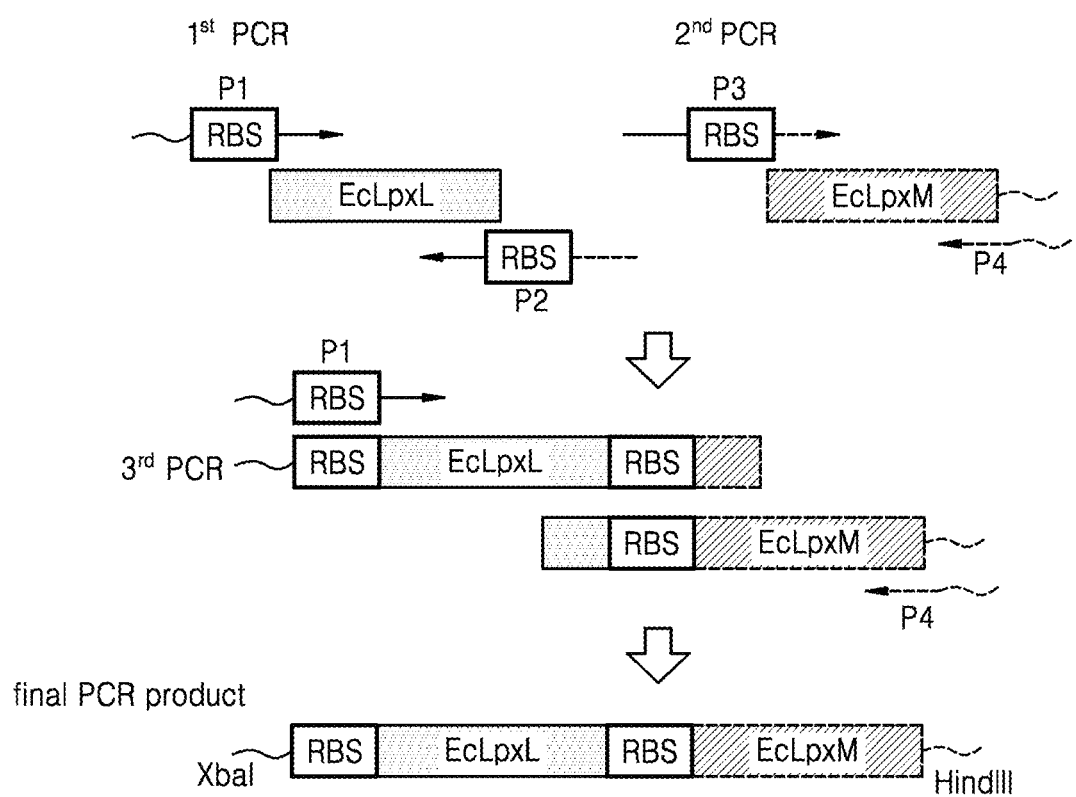
FIG. 2 is a schematic view illustrating a method of preparing a polymerase chain reaction (PCR) product including EcLpxL and EcLpxM.

To obtain a polynucleotide that encodes *E. coli* LpxM polypeptides, from the *E. coli* W3110 genome, a polynucleotide (GenBank Accession No. AP009048.1 (c1941907.1940936, SEQ ID NO: 6), which encodes an EcLpxM polypeptide (GenBank Accession No. BAA15663.1, SEQ ID NO: 5) including an RBS, was amplified by a second PCR using a pair of primers (see FIG. 2):

LpxM forward primer P3:
(SEQ ID NO: 7)
5'-GAAGGCGTTCCTTCACGCTATTAATAAGAAGGAGATATACCAA
TGGAAACGAAAAAAAATAATAGCG-3'

LpxM reverse primer P4:
(SEQ ID NO: 8)
5'-GCAGAAGCTTTTATTTGATGGGATAAAGATCTTTGCG-3'

An EcLpxLEcLpxM polynucleotide, which is a fusion of the EcLpxL polynucleotide and the EcLpxM polynucleotide, was amplified by a third PCR using the LpxL forward primer P1 and the LpxM reverse primer P4, and using the EcLpxL polynucleotide obtained from the first PCR and the EcLpxM polynucleotide obtained from the second PCR as templates.

The PCRs were performed using a KOD hot start DNA polymerase (Novagen) in a T3000 thermocycler (Biometra).

The amplified products were purified using a DokDo-Prep PCR purification kit (ELPIS-BIOTECH. Inc.), and the purified products were introduced into a pWSK29 plasmid (see Wang, R. F., and Kushner, S. R., Gene (1991), vol. 100, p. 195-199). The cloned plasmid was transformed into *E. coli* DH5α by electroporation, and the transformed *E. coli* was then selected on an LB-ampicillin plate. The cloned plasmid was named pWSK29-EcLpxLEcLpxM (see FIG. 2).

1.2. Preparation of pKHSC0004

To modify a promoter sequence of the pWSK29-EcLpxLEcLpxM into a $P_L$ promoter sequence (5'-TTGACATAAATACCACTGGCGGTGATACT-3', SEQ ID NO: 9), site-directed mutagenesis was performed using PCR with the plasmid pWSK29-EcLpxLEcLpxM prepared above in Section 1.1 as a template and a pair of primers:

```
Forward primer amplifying P_L promoter:
                                     (SEQ ID NO: 10)
5'-GGCAGTGAGCGCAACGCAGAATTCTTGACATAAATACCACTGG
CGGTGATACTTTCACACAGGAAACAGCTATGACC-3'

Reverse primer amplifying P_L promoter:
                                     (SEQ ID NO: 11)
5'-GGTCATAGCTGTTTCCTGTGTGAAAGTATCACCGCCAGTGGTA
TTTATGTCAAGAATTCTGCGTTGCGCTCACTGCC-3'
```

The PCR was performed using a Quikchange Site-Directed Mutagenesis Kit (Agilent) in a T3000 thermocycler (Biometra).

After the site-directed mutagenesis, the reaction product was treated with a Dpn1 restriction enzyme (ELPIS-BIOTECH. Inc.), then transformed into *E. coli* DH5α by electroporation, and the transformed *E. coli* was then selected on an LB-ampicillin plate. The cloned plasmid was named pKHSC0004.

1.3. Preparation of pBAD30-HμLpxE-frt-kan-frt 1.3.1. Preparation of pBAD30-HμLpxE To delete a HindIII restriction enzyme recognition site sequence in a gene hp0021 encoding *Helicobactor pylori* LpxE (HμLpxE), a nucleotide sequence encoding serine (17Ser), the 17$^{th}$ amino acid from the N-terminal, was mutated from AGC to TCG. The mutated hp0021 gene was synthesized by Integrated DNA technologies (mBiotech, Republic of Korea).

A polynucleotide (SEQ ID NO: 13) that encodes HμLpxE amino acid sequences (SEQ ID NO: 12) was amplified using the mutated hp0021 as a template and a pair of primers:

Forward primer for amplifying HμLpxE mutant: 5'-GATCCTCTAGAAAGGAGATATATTGAT-GAAAAAATTCTTATTTAAACAAAAATTT-3' (SEQ ID NO: 14)

Reverse primer for amplifying *Helicobactor pylori* LpxE mutant: 5'-AGCTACAAGCTTTTAAGGCTTTTTGGGGC-3' (SEQ ID NO: 15)

The PCR was performed using a KOD hot start DNA polymerase (Novagen) in a T3000 thermocycler (Biometra).

After the PCR, the amplified products were purified as described above in Section 1.1. The purified product was cloned into a pBAD30 plasmid (see Guzman, L. M., Belin, D., Carson, M. J., Beckwith, J., J Bacteriol (1995). 177(14), p. 4121-4130). The cloned plasmid was transformed into *E. coli* and the transformed *E. coli* was then selected as described above in Section 1.1. The cloned plasmid was named pBAD30-HμLpxE.

1.3.2. Preparation of pBAD30-HμLpxE-frt-kan-frt

A frt-kan-frt polynucleotide having HindIII restriction enzyme recognition site sequences at both terminals was amplified using a pKD4 (Kirill A. Datsenko, and Barry L. Wanner PNAS (2000), vol. 97, p. 6640-6645) plasmid as a template and a pair of primers:

Forward primer for amplifying frt-kan-frt: 5'-GCAGAAGCTTGTGTAGGCTGGAGCTGCTTC-3' (SEQ ID NO: 16)

Reverse primer for amplifying frt-kan-frt: 5'-GCAGAAGCTTATGAATATCCTCCTTAGTTCCTAT-3' (SEQ ID NO: 17)

The PCR was performed using a pfu DNA polymerase (ELPIS-BIOTECH. Inc.) in a T3000 thermocycler (Biometra).

After the PCR, the amplified product was purified as described above in Section 1.1. The purified product was then cloned into a pBAD30 plasmid as described above in Section 1.3.1. The cloned plasmid was transformed into *E. coli* and the transformed *E. coli* was then selected as described above in Section 1.1. The cloned plasmid was named pBAD30-HμLpxE-frt-kan-frt.

Example 2. Preparation of *E. coli* Strains 2.1. Preparation of *E. coli* KHSC0044 (pWSK29-EcLpxLEcLpxM, $^Δ$lpxT, $^Δ$pagP, bacA::HμLpxE, kdtA::kan, W3110) Strain 2.1.1 Preparation of *E. coli* from which lpxT Gene was Removed from Genome An *E. coli* lpxT::kan, W3110 strain was prepared in which a kanamycin cassette is inserted into an lpxT gene (SEQ ID NO: 19) of the *E. coli* genome, wherein the lpxT gene encodes an LpxT polypeptide (SEQ ID NO: 18).

Then, a pCP20 plasmid (Kirill A. Datsenko, and Barry L. Wanner PNAS (2000), vol. 97, p. 6640-6645) was transformed into the *E. coli* lpxT::kan, W3110 strain and the transformed *E. coli* was then selected on an LB plate. The selected *E. coli* was inoculated on an LB plate, and selected at a temperature of 42° C., thereby preparing an *E. coli* ΔlpxT, W3110 strain from which lpxT and the kanamycin cassette were removed.

2.1.2 Preparation of *E. coli* from which pagP Gene and lpxT Gene were Removed from Genome A P1 phage was prepared from an *E. coli* strain JW0617 (pagP::kan), Keio *E. coli* knockout library) in which a kanamycin cassette was inserted into a pagP gene of the *E. coli* genome. The P1 phage was transduced into the *E. coli* ΔlpxT, W3110 strain prepared above in Section 2.1.1, and the transduced *E. coli* was then selected on an LB-kanamycin plate, thereby preparing an *E. coli* ΔlpxT, pagP::kan, W3110 strain into which pagP::kan was inserted in place of the pagP gene.

A pCP20 plasmid as described above in Section 2.1.1 was transformed into the *E. coli* strain ΔlpxT, pagP::kan, W3110 and the transformed *E. coli* was then selected on an LB-ampicillin plate. The selected *E. coli* was inoculated on an LB plate, and selected *E. coli* then selected at a temperature of about 42° C., thereby preparing an *E. coli* $^Δ$lpxT, $^Δ$pagP, W3110 strain from which pagP and the kanamycin cassette were removed.

2.1.3 Preparation of *E. coli* from which lpxT Gene and pagP Gene were Removed from Genome and bacA Gene of Genome was Replaced by HμLpxE-frt-kan-frt Polynucleotide To prepare a bacA::HμLpxE-frt-kan-frt polynucleotide capable of homologous recombination with the bacA gene, PCR was performed using the pBAD30-HμLpxE-frt-kan-frt plasmid prepared above in Section 1.3.2 as a template and a pair of primers:

```
Forward primer amplifying bacA::HpLpxE-frt-kan-frt:
                                     (SEQ ID NO: 20)
5'-AACCTGGTCATACGCAGTAGTTCGGACAAGCGGTACATTTTAATA
ATTTAGGGGTTTATTGATGAAAAAATTCTTATTTAAACAAAAAT-3'

Reverse primer amplifying bacA::HpLpxE-frt-kan-frt:
                                     (SEQ ID NO: 21)
5'-TGACAACGCCAAGCATCCGACACTATTCCTCAATTAAAAGAACAC
GACATACACCGCAGCCGCCACATGAATATCCTCCTTAGTTCCTA-3'
```

The PCR was performed using a pfu DNA polymerase (ELPIS-BIOTECH. Inc.) in a T3000 thermocycler (Biometra).

Figure 3:
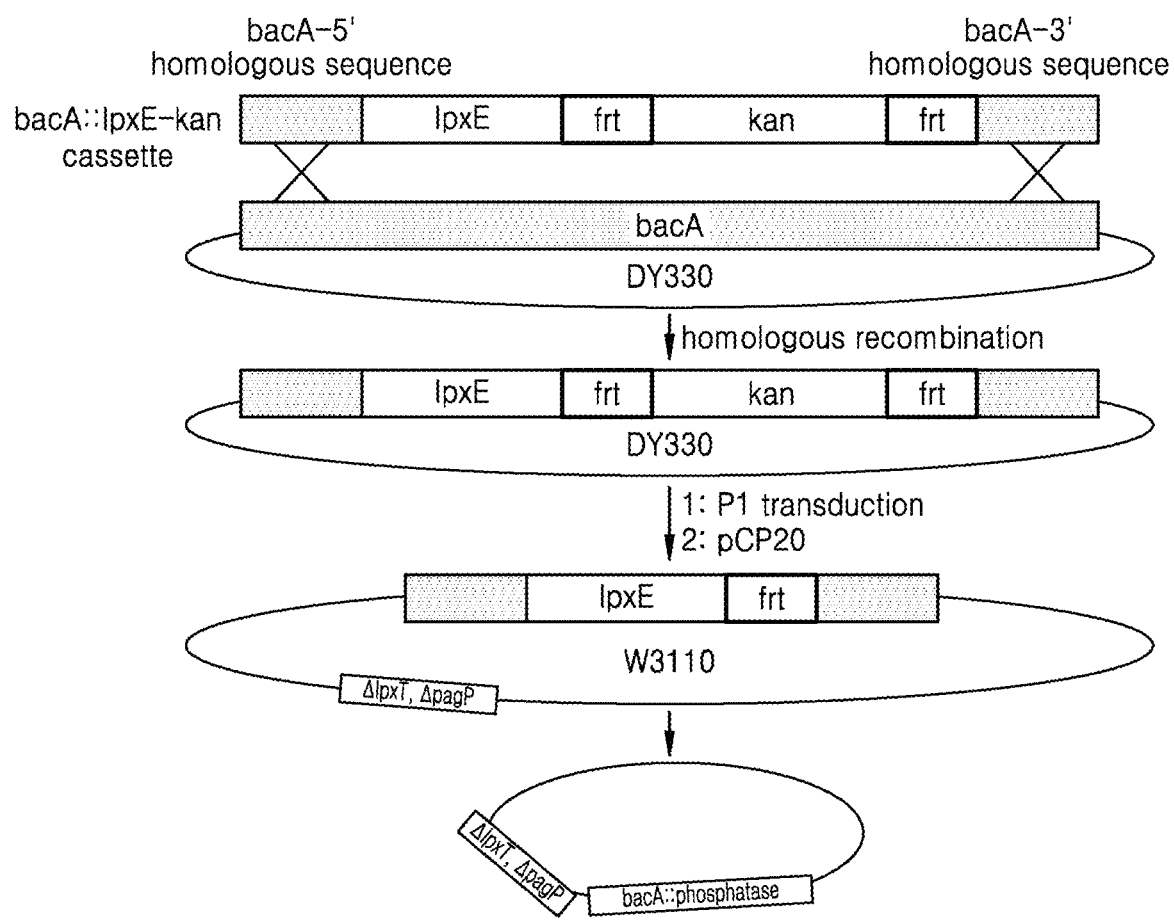
FIG. 3 is a schematic view illustrating a method of replacing bacA of an *Escherichia coli* chromosome with lpxE encoding phosphatase, by using homologous recombination.

After the PCR, the amplified product was purified as described above in Section 1.1. The purified product was then transformed into E. coli DY330 (Yu, D., et. al., PNAS. (2000). 97(11), p 5978-5983) by electroporation, thereby preparing an E. coli bacA::HµLpxE-frt-kan-frt, DY330 strain through homologous recombination with upstream and downstream neighboring sequences of the bacA gene of the DY330 genome (see FIG. 3).

A P1 phage was prepared from the E. coli bacA::HµLpxE-frt-kan-frt, DY330 strain. The P1 phage was transduced into the E. coli $^\Delta$lpxT, $^\Delta$pagP, W3110 strain prepared above in Section 2.1.2 and the transduced E. coli was then selected on an LB-kanamycin plate. The selected E. coli was named $^\Delta$lpxT, $^\Delta$pagP, bacA::HµLpxE-frt-kan-frt, W3110 (see FIG. 3).

Figure 4:
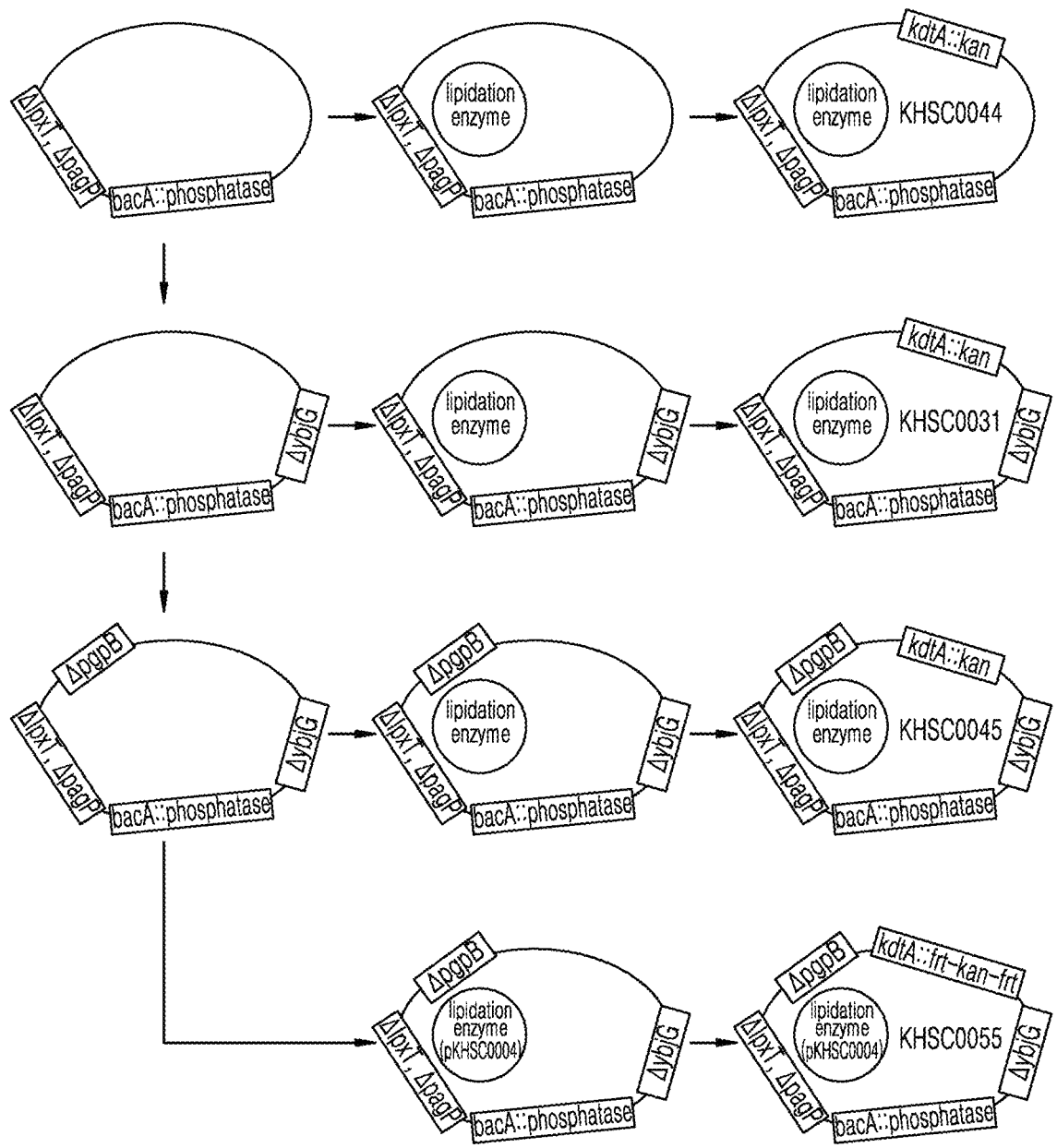
FIG. 4 is a schematic view illustrating a process of constructing a strain in which the stability of a phosphatase gene inserted into its chromosome is stabilized.

2.1.4 Preparation of E. coli from which lpxT Gene and pagP Gene were Removed from Genome and bacA Gene of Genome was Replaced by HµLpxE Gene A pCP20 plasmid as described above in Section 2.1.1 was transformed into the E. coli $^\Delta$lpxT, $^\Delta$pagP, bacA::HµLpxE-frt-kan-frt, W3110 strain prepared above in Section 2.1.3, and the transformed E. coli was then selected on an LB-ampicillin plate. The selected E. coli was inoculated on an LB plate, and selected at a temperature of about 42° C., thereby preparing an E. coli $^\Delta$lpxT, $^\Delta$pagP, bacA::HµLpxE, W3110 strain from which bacA and the kanamycin cassette were removed, and into which HµLpxE was introduced (see FIG. 3 and the left region of the first row of FIG. 4).

2.1.5 Preparation of E. coli pWSK29-EcLpxLEcLpxM, $^\Delta$lpxT, $^\Delta$pagP, bacA::HµLpxE, W3110 Strain The pWSK29-EcLpxLEcLpxM plasmid prepared above in Section 1.1 was transformed into the E. coli $^\Delta$lpxT, $^\Delta$pagP, bacA::HµLpxE, W3110 strain prepared above in Section 2.1.4 by electroporation. The transformed E. coli was then selected on, thereby preparing an E. coli pWSK29-EcLpxLEcLpxM, $^\Delta$lpxT, $^\Delta$pagP, bacA::HµLpxE, W3110 strain (see the middle region of the first row of FIG. 4).

2.1.6 Preparation of E. coli KHSC0044 Strain

A P1 phage was prepared from an E. coli HSC1/pEcKdt strain having the kanamycin cassette inserted into a kdtA gene (SEQ ID NO: 23) encoding a KdtA polypeptide (SEQ ID NO: 22) in the E. coli chromosome, and including a pEcKdtA plasmid (Chung, H. S., and Raetz, C. R., Biochemistry (2010), vol. 49(19), p. 4126-4137). The P1 phage was transduced into the E. coli pWSK29-EcLpxLEcLpxM, $^\Delta$lpxT, $^\Delta$pagP, bacA::HµLpxE, W3110 strain prepared above in section 2.1.5 (see FIG. 3), and this E. coli was then selected on. The selected E. coli was named E. coli KHSC0044 (pWSK29-EcLpxLEcLpxM, $^\Delta$lpxT, $^\Delta$pagP, bacA::HµLpxE, kdtA::kan, W3110) (see the right region of the first row of FIG. 4).

2.2. Preparation of E. coli KHSC0031 (pWSK29-EcLpx-LEcLpxM, $^\Delta$lpxT, $^\Delta$pagP, $^\Delta$ybjG, b$_a$cA::HµLpxE, kdtA::kan, W3110) Strain 2.2.1 Preparation of E. coli from which lpxT Gene, pagP Gene, and ybjG Gene was Removed from Genome and bacA of Genome was Replaced by HµLpxE Gene A P1 phage was prepared from an E. coli strain JW5112 (ybjG::kan) (Keio E. coli knockout library) in which a kanamycin cassette was inserted into an ybjG gene of the E. coli genome. The P1 phage was transduced into the E. coli $^\Delta$lpxT, $^\Delta$pagP, bacA::HµLpxE, W3110 strain prepared above in Section 2.1.4, and this E. coli was then selected on an LB-kanamycin plate, thereby preparing an E. coli strain $^\Delta$lpxT, $^\Delta$pagP, bacA::HµLpxE, ybjG::kan, W3110 in which ybjG::kan was inserted in place of the ybjG gene.

A pCP20 plasmid as described above in Section 2.1.1 was transformed into the E. coli $^\Delta$lpxT, $^\Delta$pagP, bacA::HµLpxE, ybjG::kan, W3110 strain, and the transformed E. coli was then selected on an LB-ampicillin plate. The selected E. coli was inoculated on an LB-ampicillin plate, selected at a temperature of about 42° C., thereby preparing an E. coli strain $^\Delta$lpxT, $^\Delta$pagP, $^\Delta$ybjG, bacA::HµLpxE, W3110 from which ybjG and the kanamycin cassette were removed (see the left region of the second row of FIG. 4)

2.2.2 Preparation of E. coli pWSK29-EcLpxLEcLpxM, $^\Delta$lpxT, $^\Delta$pagP, $^\Delta$ybjG, bacA::HµLpxE, kdtA::kan, W3110 Strain The pWSK29-EcLpxLEcLpxM plasmid prepared as described above in Section 1.1 was transformed into the E. coli $^\Delta$lpxT, $^\Delta$pagP, $^\Delta$ybjG, bacA::HµLpxE, W3110, prepared as described above in Section 2.2.1, by electroporation. The transformed E. coli was selected on an LB-ampicillin plate, thereby preparing an E. coli pWSK29-EcLpxLEcLpxM, $^\Delta$lpxT, $^\Delta$pagP, $^\Delta$ybjG, bacA::HµLpxE, W3110 strain (see the middle region of the second row of FIG. 4).

2.2.3 Preparation of E. coli KHSC0031 Strain

A P1 phage was prepared from the E. coli HSC1/pEcKdt as described above in Section 2.1.6. The P1 phage was transduced into the E. coli pWSK29-EcLpxLEcLpxM, $^\Delta$lpxT, $^\Delta$pagP, $^\Delta$ybjG, bacA::HµLpxE, W3110 strain as prepared in Section 2.2.2, and the transformed E. coli was then selected on an LB-kanamycin/ampicillin plate. The selected E. coli was named KHSC0031 (pWSK29-EcLpxLEcLpxM, $^\Delta$lpxT, $^\Delta$pagP, $^\Delta$ybjG, bacA::HµLpxE, kdtA::kan, W3110) (see the right region of the second row of FIG. 4).

2.3. Preparation of E. coli KHSC0045 (pWSK29-EcLpx-LEcLpxM, $^\Delta$lpxT, $^\Delta$pagP, $^\Delta$ybjG, pgpB, bacA::HµLpxE, kdtA::kan, W3110) Strain 2.3.1 Preparation of E. coli from which lpxT, pagP, ybjG, and pgpB Genes were Removed from Genome and bacA Gene of Genome was replaced by HµLpxE Gene A P1 phage was prepared from an E. coli strain JW1270 (pgpB::kan) (Keio E. coli knockout library) in which a kanamycin cassette as inserted into a pgpB gene of the E. coli genome. The P1 phage was transduced into the E. coli $^\Delta$lpxT, $^\Delta$pagP, $^\Delta$ybjG,, bacA::HµLpxE, W3110 prepared in Section 2.2.1, and the transduced E. coli was then selected on an LB-kanamycin plate, thereby preparing an E. coli strain $^\Delta$lpxT, $^\Delta$pagP, $^\Delta$ybjG, bacA::HµLpxE, pgpB::kan W3110 in which pgpB::kan was inserted in place of the pgpB gene.

A pCP20 plasmid as described above in Section 2.1.1 was transformed into the E. coli strain $^\Delta$lpxT, $^\Delta$pagP, $^\Delta$ybjG, bacA::HµLpxE, pgpB::kan, W3110, and the transformed E. coli was then selected on an LB-ampicillin plate. The selected E. coli was inoculated on an LB plate, and then selected at a temperature of about 42° C., thereby preparing an E. coli strain $^\Delta$lpxT, $^\Delta$pagP, $^\Delta$ybjG, pgpB, bacA::HµLpxE, W3110 in which pgpB and the kanamycin cassette were removed (see the left region of the third row of FIG. 4).

2.3.2 Preparation of E. coli pWSK29-EcLpxLEcLpxM, $^\Delta$lpxT, $^\Delta$pagP, $^\Delta$ybjG, $^\Delta$pgpB, bacA::HµLpxE, kdtA::kan, W3110 Strain The pWSK29-EcLpxLEcLpxM plasmid prepared as described above in Section 1.1 was transformed into the E. coli $^\Delta$lpxT, $^\Delta$pagP, $^\Delta$ybjG, $^\Delta$pgpB, bacA::HµLpxE, W3110, prepared as described above in Section 2.3.1, by electroporation. The transformed E. coli was selected on an LB-ampicillin plate, thereby preparing an E. coli pWSK29-EcLpxLEcLpxM, $^\Delta$lpxT, $^\Delta$pagP, $^\Delta$ybjG, $^\Delta$pgpB, bacA:: HµLpxE, W3110 strain (see the middle region of the third row of FIG. 4).

2.3.3 Preparation of E. coli KHSC0045 Strain

A P1 phage was prepared from the E. coli HSC1/pEcKdt as described above in Section 2.1.6 (Chung, H. S., and Raetz, C. R., Biochemistry (2010), vol. 49(19), p. 4126-4137). The P1 phage was transduced into the E. coli pWSK29-EcLpxLEcLpxM, $^\Delta$lpxT, $^\Delta$pagP, $^\Delta$ybjG, $^\Delta$pgpB, bacA::HµLpxE, W3110 strain as prepared in Section 2.3.2, and this E. coli was then selected on an LB-kanamycin/ampicillin plate. The selected E. coli was named KHSC0045 (pWSK29-EcLpxLEcLpxM, $^\Delta$lpxT, $^\Delta$pagP, $^\Delta$ybjG, $^\Delta$pgpB, bacA::HµLpxE, kdtA::kan, W3110) (see the right region of the third row of FIG. 4). The KHSC0045 strain has been deposited in the Korea Research Institute of Bioscience and Biotechnology, which is an international depository authority under the Budapest Treaty as of Jul. 6, 2017 (Accession Number: KCTC 13296BP).

2.4. Preparation of E. coli KHSC0055 (pKHSC0004, $^\Delta$lpxT, $^\Delta$pagP, $^\Delta$ybjG, $^\Delta$pgpB, bacA::HµLpxE, kdtA::kan, W3110) Strain 2.4.1 Preparation of E. coli pKHSC0004, $^\Delta$lpxT, $^\Delta$pagP, $^\Delta$ybjG, $^\Delta$pgpB, bacA::HµLpxE, kdtA::kan, W3110 Strain The pKHSC0004 plasmid prepared above in Section 1.2 was transformed into the E. coli $^\Delta$lpxT, $^\Delta$pagP, $^\Delta$ybjG, $^\Delta$pgpB, bacA::HµLpxE, W3110 strain prepared above in Section 2.3.1. The transformed E. coli was selected on an LB-ampicillin plate, thereby preparing an E. coli pKHSC0004, $^\Delta$lpxT, $^\Delta$pagP, $^\Delta$ybjG, $^\Delta$pgpB, bacA::HµLpxE, W3110 strain (see the left region of the fourth row of FIG. 4).

2.4.2 Preparation of E. coli KHSC0055 Strain

An E. coli strain KHSC0055 including a pEcKdtA plasmid and a kanamycin cassette (frt-kan-frt) inserted into a kdtA gene (SEQ ID NO: 23) encoding a KdtA polypeptide (SEQ ID NO: 22) in the E. coli chromosome was prepared in the following manner.

A kdtA::frt-kan-frt polynucleotide capable of homologous recombination with the kdtA gene was amplified using a pKD4 plasmid (Kirill A. Datsenko, and Barry L. Wanner PNAS(2000), vol. 97, p. 6640-6645) as a template and a pair of primers:

Forward primer amplifying kdtA::frt-kan-frt: 5'-GCTAAATACATAGAATCCCCAGCACATC-CATAAGTCAGCTATTTACTATGCTCGAATTGCGTG-TAGGCTGGAGCTGCTTC-3' (SEQ ID NO: 24)

Reverse primer amplifying kdtA::frt-kan-frt: 5'-ATCGA-TATGACCATTGGTAATGGGATCGAAAGTACCCGGA-TAAATCGCCCGTTTTTGCATTGAATATCCTCCT-TAGTTCCTATTCC-3' (SEQ ID NO: 25)

The PCR was performed using a pfu DNA polymerase (ELPIS-BIOTECH. Inc.) in a T3000 thermocycler (Biometra).

After the PCR, the amplified product was purified as described above in Section 1.1. The purified product was then transformed into E. coli DY330 including the pEcKdtA plasmid (Chung, H. S., and Raetz, C. R., Biochemistry (2010), vol. 49(19), p. 4126-4137) by electroporation, thereby preparing an E. coli pEcKdtA, kdtA::frt-kan-frt, DY330 strain through homologous recombination with upstream and downstream neighboring sequences of the kdtA gene of the DY330 genome (see FIG. 3).

A P1 phage was prepared from the E. coli pEcKdtA, kdtA:lrt-kan-frt, DY330. The P1 phage was transduced into the E. coli pKHSC0004, $^\Delta$lpxT, $^\Delta$pagP, $^\Delta$ybjG, $^\Delta$pgpB, bacA::HµLpxE, W3110 strain prepared in Section 2.4.1, and the transduced E. coli was then selected on an LB-kanamycin plate. The selected E. coli was named KHSC0055 (pKHSC0004, $^\Delta$lpxT, $^\Delta$pagP, $^\Delta$ybjG, $^\Delta$pgpB, bacA::HµLpxE, kdtA::frt-kan-frt, W3110) (see the right region of the fourth row of FIG. 4).). The KHSC0055 strain has been deposited in the Korea Research Institute of Bioscience and Biotechnology, which is an international depository authority under the Budapest Treaty as of Jul. 6, 2017 (Accession Number: KCTC 13297BP).

Example 3. Determination of Lipid Compositions of E. coli Strains KHSC0044, KHSC31, KHSC0045, and KHSC0055

3.1 Cultures of KHSC0044, KHSC0031, and KHSC0045

E. coli strains KHSC0044, KHSC0031, and KHSC0045 were prepared as described above in Section 2.1.6, Section 2.2.3, and Section 2.3.3, respectively.

A stock of each of the E. coli strains was inoculated on an LB plate containing 50 µg/mL of ampicillin (EMD millipore) and 1 mM of isopropyl β-D-1-thiogalactopyranoside (IPTG) (UBP Bio), and then cultured. KHSC0044 (8 colonies), KHSC0031 (7 colonies), and KHSC0045 (7 colonies) strains were selected, and then each inoculated into 3 mL of an LB liquid medium containing 50 µg/mL of ampicillin (EMD millipore) and 1 mM of IPTG, and then cultured overnight at about 30° C. Each resulting culture solution was inoculated into 200 mL of a fresh) LB liquid medium containing 50 µg/mL of ampicillin and 1 mM of IPTG, diluted to an $OD_{600}$ of about 0.06 to about 0.1, and then cultured overnight at about 30° C.

3.2 Culture of KHSC0055

E. coli KHSC0055 strain was prepared as described above in Section 2.4.2.

A KHSC0055 stock was inoculated into 3 mL of an LB liquid medium with/without 50 µg/mL of ampicillin, and then incubated overnight at about 30° C. The resulting culture solution was inoculated into 200 mL of a fresh LB liquid medium with/without 50 µg/mL of ampicillin and then incubated overnight at about 30° C.

3.3 Lipid Extraction from E. coli KHSC0044, KHSC0031, KHSC0045, and KHSC0055 Strains The E. coli culture media obtained as described above in Section 3.1 and Section 3.2 were each centrifuged at room temperature at about 4000×g for about 20 minutes to obtain the E. coli strains. The obtained E. coli strains were each washed with 30 mL of PBS and then resuspended in 8 mL of PBS.

10 mL of chloroform and 20 mL of methanol were added to the resuspended E. coli, and then incubated at room temperature for about 1 hour with occasional shaking. Subsequently, the incubated mixture was centrifuged at room temperature at a speed of 2500×g for about 30 minutes to collect a supernatant. 10 mL of chloroform and 10 mL of water were added to the collected supernatant, mixed completely, and then centrifuged at room temperature at 2500×g for about 20 minutes. After an organic solvent layer was isolated from the centrifuged mixture, the organic solvent layer was extracted twice by adding a pre-equilibrated organic solvent layer to the upper aqueous layer. The organic solvent layer was pooled, and then dried in a rotary evaporator to obtain lipids. The obtained lipids were dissolved in 5 mL of a 4:1 (v/v) mixture of chloroform and methanol, and then subjected to ultrasonic irradiation in a water bath. The ultrasonically irradiated lipids were moved to a new test tube, and the obtained lipid s were dried at room temperature in a nitrogen gas environment and then stored at about −80° C.

3.4. Lipid Analysis by Thin Layer Chromatography (TLC)

Figure 5:
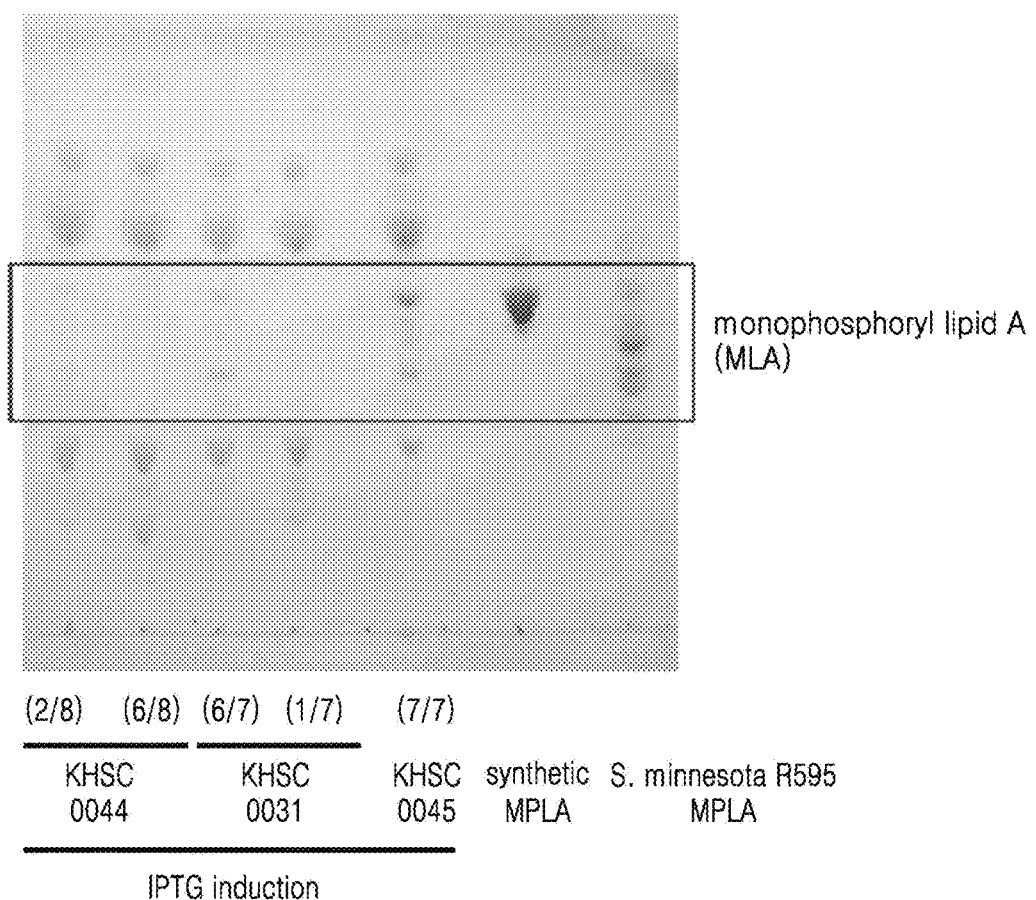
FIG. 5 is an image showing thin layer chromatography (TLC) results of lipids extracted from *E. coli* strains in which bacA of the *Escherichia coli* genome was removed and replaced with a phosphatase gene, wherein Lane 1 represents KHSC0044 producing 1-dephospho-lipid A (two of the 8 colonies cultured in the same cell stock), Lane 2 represents KHSC0044 not producing 1-dephospho-lipid A (six of the 8 colonies cultured in the same cell stock), Lane 3 represents KHSC0031 producing 1-dephospho-lipid A (six of the 7 colonies cultured in the same cell stock), Lane 4 represents KHSC0031 not producing 1-dephospho-lipid A (one of the 7 colonies cultured in the same cell stock), Lane 5 represents KHSC0045 stably producing 1-dephospho-lipid A (all of the 7 colonies cultured in the same cell stock) with the highest yield, Lane 6 represents synthetic 1-dephospho-hexa acylated lipid A (InvovoGen), and Lane 7 represents 1-dephospho-lipid A separated and purified from *Salmonella minnesota* R595 after acid-base hydrolysis (InvovoGen)

Membrane lipids of each *E. coli* strain obtained as described above in Section 3.3 was analyzed using, as positive control groups, MPLA Synthetic (InvovoGen, Catalog Code: tlrl-mpls, synthetic 1-dephospho-hexa acylated lipid A (Lane 6 of FIG. 5, and Lane 1 of FIG. 6), and MPLA-SM (InvovoGen, Catalog Code tlrl-mpla, 1-dephospho-lipid A separated and purified from lipopolysaccharides (LPS) of *Salmonella minnesota* R595 after acid-based hydrolysis) (Lane 7 of FIG. 5).

To perform thin layer chromatography (TLC), as described above in Section 3.2, lipid was obtained from 200 mL of each *E. coli* culture solution, and one-third of the obtained total liquid was dissolved in 200 μL of a 4:1 (v/v) mixture of chloroform and methanol. Subsequently, about 5 μL to 15 μL of the mixture was spotted on a 10×10 cm high-performance TLC (HPTLC) plate (EMD Chemicals) and developed in a solvent mixture of chloroform, methanol, water, and ammonium hydroxide (28% (v/v) ammonia) in a ratio of 40:25:4:2 (v/v). The developed plate was then dried, visualized by spraying with 10% (v/v) of sulfuric acid (in ethanol), and then heated on a hot plate of 300° C. The TLC results of the liquids are shown in FIGS. 5, 6, and 7.

FIG. 5 is an image showing TLC results of lipids extracted from the *E. coli* strains from which bacA gene of the *E. coli* genome was removed and replaced with a phosphatase gene. In FIG. 5, Lane 1 represents KHSC0044 producing 1-dephospho-lipid A (two of the 8 colonies cultured in the same cell stock), Lane 2 represents KHSC0044 not producing 1-dephospho-lipid A (six of the 8 colonies cultured in the same cell stock, Lane 3 represents KHSC0031 producing 1-dephospho-lipid A (six of the 7 colonies cultured in the same cell stock), Lane 4 represents KHSC0031 not producing 1-dephospho-lipid A (one of the 7 colonies cultured in the same cell stock), Lane 5 represents KHSC0045 stably producing 1-dephospho-lipid A (all of the 7 colonies cultured in the same cell stock, Lane 6 represents the synthetic 1-dephospho-hexa acylated lipid A (InvovoGen, Catalog Code: tlrl-mpls), and Lane 7 represents 1-dephospho-lipid A separated and purified from *Salmonella minnesota* R595 after acid-base hydrolysis (InvovoGen, Catalog Code: firl-mpla).

Figure 6:
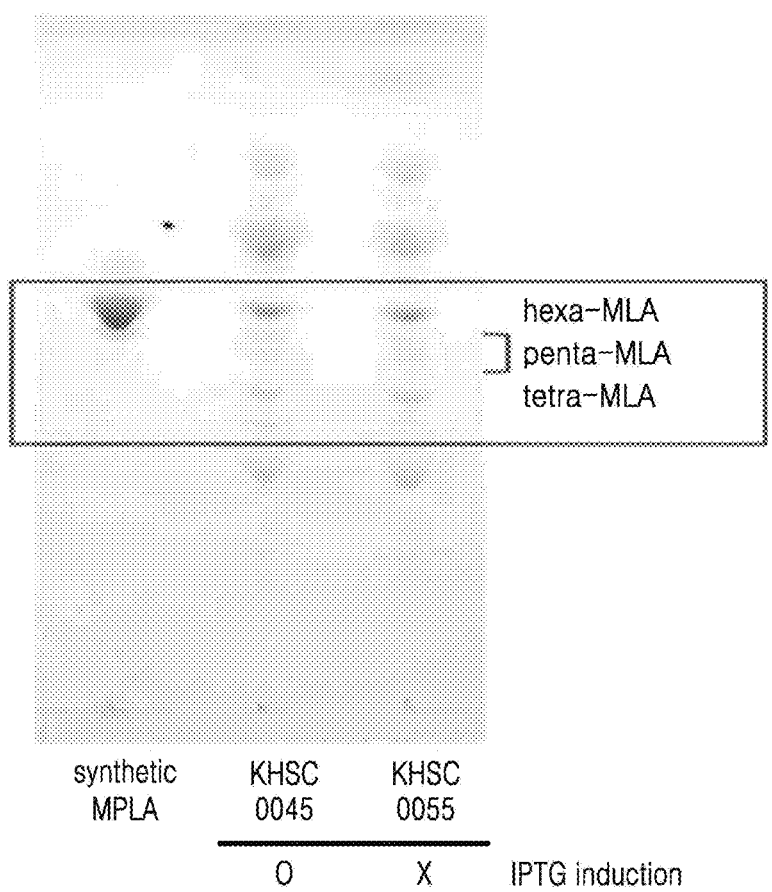
FIG. 6 is an image showing TLC results of lipids of *Escherichia coli* strains KHSC0045 and KHSC0055, wherein Lane 1 represents the synthetic 1-dephospho-hexa acylated lipid A (InvovoGen), and Lane 2 represents KHSC0045 cultured with an overexpression inducer which induces overexpression of a lipidation enzyme, and Lane 3 represents KHSC0055 cultured without use of an overexpression inducer.

FIG. 6 is an image showing TLC results of the lipids of the *E. coli* strains KHSC0045 and KHSC0055. In FIG. 6, Lane 1 represents the synthetic 1-dephospho-hexa acylated lipid A (InvovoGen, Catalog Code: tlrl-mpls), Lane 2 represents KHSC0045 cultured with an overexpression inducer to induce overexpression of a lipidation enzyme, and Lane 3 represents KHSC0055 cultured without use of an overexpression inducer.

Figure 7:
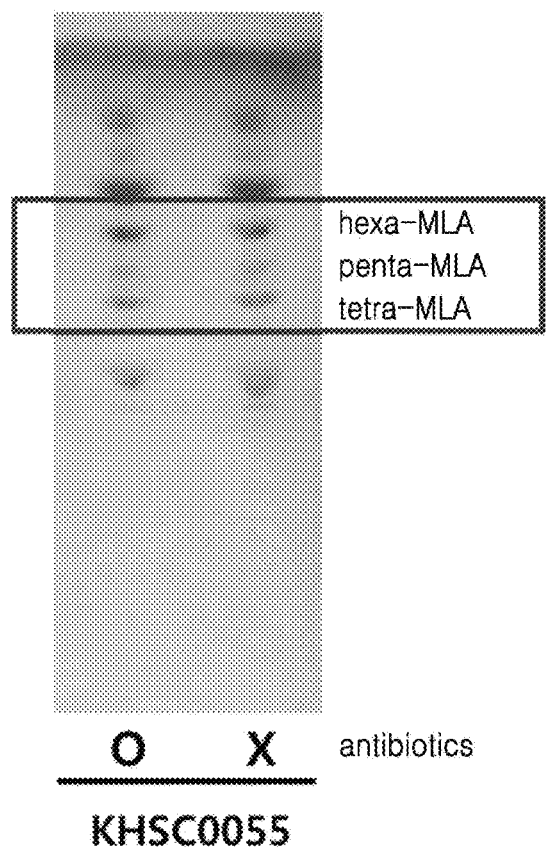
FIG. 7 is an image showing TLC results of lipids of *Escherichia coli* strains KHSC0045 and KHSC0055, wherein Lane 1 represents KHSC0055 cultured with an antibiotics, and Lane 3 represents KHSC0055 cultured without use of the antibiotics.

FIG. 7 is an image showing TLC results of lipids of *E. coli* strains KHSC0045 and KHSC0055, wherein Lane 1 represents KHSC0055 cultured with an antibiotics, and Lane 3 represents KHSC0055 cultured without use of the antibiotics.

Referring to FIG. 5, even though the cell stocks of KHSC0044 and KHSC0031 were each derived from one colony, the selected 8 colonies of KHSC0044 were found to include colonies in which 1-dephospho-lipid A was detected (Lane 1, two of the 8 colonies), and colonies in which 1-dephospho-lipid A was not detected (Lane 2, six of the 8 colonies), and the selected 7 colonies of KHSC0031 were found to include colonies in which 1-dephospho-lipid A was detected (Lane 3, six of the 7 colonies) and a colony in which 1-dephospho-lipid A was not detected (Lane 4, one of the 7 colonies). However, 1-dephospho-lipid A was detected in all of the selected 7 colonies of KHSC0045 (Lane 5).

These results indicate that when a phosphatase is inserted into the genome of *E. coli*, an *E. coli* strain producing 1-dephospho-lipid A may inactivate the activity of the inserted phosphatase, thereby forming easily natural mutant that cannot produce 1-dephospho-lipid A.

Therefore, it was found that, to produce 1-dephospho-lipid A by insertion of a phosphatase into the genome of *E. coli*, removing an undecaprenyl pyrophosphate phosphatase (Und-PP phosphatase) gene (bacA, pgpB, or ybjG) or phosphatidylglycerophosphate phosphatase (PGP phosphatase) gene (pgpB, pgpA, or pgpC), which are present in the genome of *E. coli*, or a combination of these genes (Lane 1, Lane 3, or Lane 5 of FIG. 5), is necessary to stably produce 1-dephospho-lipid A from *E. coli* and yield live *E. coli* with a reduced probability of natural mutation.

For the *E. coli* KHSC0045, overexpression of a lipidation enzyme during incubation of the strain is necessary to effectively produce 1-dephospho-hexa acylated lipid A. As a result of the membrane lipid composition comparison using the synthetic 1-dephospho-hexa acylated lipid A (Lane 1 of FIG. 6) and KHSC0045 incubated by inducing the overexpression of a lipidation enzyme with an overexpression inducer as positive control groups, the *E. coli* KHSC0055 transformed into pKHSC0004 was found to be a live *E. coli* strain effectively producing 1-dephospho-hexa acylated lipid A (Lane 3 of FIG. 6) without use of an overexpression inducer (Lane 3 of FIG. 6).

For the *E. coli* KHSC0055, while the plasmid pKHSC0004 stably sustained in the *E. coli* KHSC0055, the *E. coli* KHSC0055 effectively produced 1-dephospho-hexa acylated lipid A with antibiotics (Lane 1 of FIG. 7) or without use of the antibiotics (Lane 2 of FIG. 7)

As described above, according to the one or more embodiments, a bacterium that constitutively produces MLA and a method of producing MLA by using the bacterium may simply produce MLA and a derivative thereof without acid hydrolysis, have a reduced probability of natural mutation, and produce increased yields of MLA and a derivative thereof by constitutive expression of the MLA and derivative thereof.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A recombinant bacterium that constitutively produces monophosphoryl lipid A (MLA) not conjugated to 2-keto-3-deoxy-D-manno-octulosonate (Kdo) moiety, wherein the recombinant bacterium comprises
   (a) (i) a genetic modification that increases the copy number of a gene encoding Lipid A 1-phosphatase (LpxE) polypeptide, (ii) at least one exogenous polynucleotide encoding a LpxE polypeptide, or (iii) a genetic modification wherein the endogenous promoter of an endogenous polynucleotide encoding a LpxE polypeptide is replaced with a heterologous promoter,
   (b) a chromosomal mutation that is a disruption in an endogenous polynucleotide that encodes an undecaprenyl pyrophosphate phosphatase (Und-PP phosphatase), and a chromosomal mutation that is a disruption in an endogenous polynucleotide that encodes a phosphatidylglycerophosphate phosphatase (PGP phosphatase), and
   (c) a mutation that is a disruption in an endogenous polynucleotide that encodes a 3-deoxy-D-manno-octulosonic acid transferase (KdtA) polypeptide.

2. The recombinant bacterium of claim 1, wherein the MLA comprises 1-dephospho-hexa-acylated lipid A, 1-dephospho-tetra-acylated lipid A, 1-dephospho-penta-acylated lipid A, or a combination thereof.

3. The recombinant bacterium of claim 1, wherein a polynucleotide that encodes the LpxE polypeptide is present in the chromosome of the recombinant bacterium.

4. The recombinant bacterium of claim 1, wherein the polynucleotide that encodes the Und-PP phosphatase is at least one selected from the group consisting of an E. coli bacA gene, an E. coli pgpB gene, and an E. coli ybjG gene.

5. The recombinant bacterium of claim 1, wherein the polynucleotide that encodes the PGP phosphatase is at least one selected from the group consisting of an E. coli pgpB gene, an E. coli pgpA gene, and an E. coli pgpC gene.

6. The recombinant bacterium of claim 1, wherein the recombinant bacterium has a disruption in an E. coli bacA gene, a disruption in an E. coli pgpB gene, and a disruption in an E. coli ybjG gene.

7. The recombinant bacterium of claim 1, wherein the mutation is a deletion, an insertion, a point mutation, a frameshift mutation, or a combination thereof.

8. The recombinant bacterium of claim 7, wherein the point mutation is a missense mutation or a nonsense mutation.

9. The recombinant bacterium of claim 1, wherein the recombinant bacterium further comprises an exogenous polynucleotide that encodes a polypeptide selected from the group consisting of a lipid A biosynthesis lauroyltransferase (LpxL) polypeptide, a lipid A biosynthesis myristoyltransferase (LpxM) polypeptide, and a combination thereof.

10. The recombinant bacterium of claim 9, wherein the polynucleotide is inducible or constitutively expressed.

11. The recombinant bacterium of claim 9, wherein the polynucleotide is expressed by a promoter selected from the group consisting of a PL promoter, a PR promoter, and a PR' promoter.

12. The recombinant bacterium of claim 1, further comprising (i) a mutation that is a disruption in an endogenous polynucleotide that encodes a Lipid A 1-diphosphate synthase (LpxT) polypeptide, (ii) a mutation that is a disruption in an endogenous polynucleotide that encodes a lipid A palmitoyltransferase (PagP) polypeptide, and (iii) a combination thereof.

13. The recombinant bacterium of claim 1, wherein the recombinant bacterium produces the MLA without induction of expression by an expression inducer, an expression-inducing stimulus, or a combination thereof.

14. The recombinant bacterium of claim 13, wherein the expression inducer is isopropyl β-D-1-thiogalactopyranoside (IPTG).

15. The recombinant bacterium of claim 1, wherein the recombinant bacterium produces the MLA in the presence of or in the absence of antibiotics.

16. A method of producing monophosphoryl lipid A (MLA), the method comprising:
    culturing the recombinant bacterium according to claim 1 to obtain a culture;

collecting the recombinant bacterium from the culture; and isolating MLA from the collected recombinant bacterium.

17. The method of claim 16, wherein the culturing of the recombinant bacterium is performed without an expression inducer, an expression-inducing stimulus, or a combination thereof.

18. The method of claim 16, wherein the culturing of the recombinant bacterium is performed in the presence of or in the absence of antibiotics.

19. A method of producing monophosphoryl lipid A (MLA), the method comprising:
culturing the recombinant bacterium according to claim 2 to obtain a culture;
collecting the recombinant bacterium from the culture; and
isolating MLA from the collected recombinant bacterium.

20. A method of producing monophosphoryl lipid A (MLA), the method comprising:
culturing the recombinant bacterium according to claim 3 to obtain a culture;
collecting the recombinant bacterium from the culture; and
isolating MLA from the collected recombinant bacterium.

* * * * *

UNITED STATES PATENT AND TRADEMARK OFFICE
CERTIFICATE OF CORRECTION

PATENT NO. : 10,557,156 B2
APPLICATION NO. : 16/026796
DATED : February 11, 2020
INVENTOR(S) : Hak Suk Chung et al.

It is certified that error appears in the above-identified patent and that said Letters Patent is hereby corrected as shown below:

On the Title Page

Item (72), Inventors 2 and 3:
Please change "Yu Hyun Ji" to -- Yuhyun Ji --
And "Jin Su An" to -- Jinsu An --

Signed and Sealed this
Thirty-first Day of March, 2020

Andrei Iancu
*Director of the United States Patent and Trademark Office*